(12) United States Patent
Luu et al.

(10) Patent No.: US 11,957,929 B2
(45) Date of Patent: Apr. 16, 2024

(54) METHODS AND APPARATUS FOR PHOTOTHERAPY

(71) Applicant: Incando Therapeutics Pte. Ltd., Singapore (SG)

(72) Inventors: Percy Luu, Singapore (SG); Cheng-Wei Pei, Belmont, CA (US); James Marshall Robinson, Hyattsville, MD (US)

(73) Assignee: INCANDO THERAPEUTICS PTE. LTD., Singapore (SG)

( * ) Notice: Subject to any disclaimer, the term of this patent is extended or adjusted under 35 U.S.C. 154(b) by 82 days.

(21) Appl. No.: 17/447,100

(22) Filed: Sep. 8, 2021

(65) Prior Publication Data

US 2021/0402202 A1 Dec. 30, 2021

Related U.S. Application Data

(63) Continuation of application No. 17/076,171, filed on Oct. 21, 2020, now Pat. No. 11,141,602.

(60) Provisional application No. 62/923,738, filed on Oct. 21, 2019.

(51) Int. Cl.
*A61N 5/06* (2006.01)

(52) U.S. Cl.
CPC ......... *A61N 5/0601* (2013.01); *A61N 5/0613* (2013.01); *A61N 2005/063* (2013.01); *A61N 2005/0664* (2013.01)

(58) Field of Classification Search
CPC ...... A61N 5/06; A61N 5/0601; A61N 5/0613; A61N 5/062; A61N 5/0622; A61N 2005/063; A61N 2005/0632; A61N 2005/0643; A61N 2005/065;
(Continued)

(56) References Cited

U.S. PATENT DOCUMENTS

| 5,766,234 A | * | 6/1998 | Chen ................ A61B 17/00234 606/14 |
| 6,231,516 B1 | | 5/2001 | Keilman et al. |
| 8,475,506 B1 | | 7/2013 | Bendett et al. |

(Continued)

FOREIGN PATENT DOCUMENTS

| CN | 114929333 A | 8/2022 |
| FR | 3010321 A1 | 3/2015 |

(Continued)

OTHER PUBLICATIONS

"European Application Serial No. 20878695.4, Response to Communication pursuant to Rules 161 and 162 filed Nov. 17, 2022", 10 pgs.

(Continued)

*Primary Examiner* — Ahmed M Farah
(74) *Attorney, Agent, or Firm* — SCHWEGMAN LUNDBERG & WOESSNER, P.A.

(57) ABSTRACT

An implantable phototherapy device includes a power receiver element configured to receive power from an external power transmitter, a light delivery element powered by the power receiver, and configured to deliver phototherapy to a target treatment area, and a tether element is coupled to the light delivery element and the power receiver element. The tether element is configured to deliver power between the power receiver element and the light delivery element.

12 Claims, 21 Drawing Sheets

(58) Field of Classification Search
CPC .... A61N 2005/0651; A61N 2005/0664; A61N 2005/067
USPC .......................... 607/88, 89, 92, 93; 128/898
See application file for complete search history.

(56) References Cited

U.S. PATENT DOCUMENTS

| | | | |
|---|---|---|---|
| 8,821,559 B2 | 9/2014 | Dimauro et al. | |
| 8,936,630 B2 | 1/2015 | Denison et al. | |
| 9,700,736 B2 | 7/2017 | Seymour et al. | |
| 10,434,327 B2 | 10/2019 | Deisseroth et al. | |
| 10,589,124 B2 | 3/2020 | Smith et al. | |
| 11,141,602 B2 | 10/2021 | Luu et al. | |
| 11,660,462 B2 * | 5/2023 | Halatsch | A61N 5/0613 606/14 |
| 2006/0100679 A1 * | 5/2006 | DiMauro | A61N 5/0601 607/94 |
| 2007/0142880 A1 | 6/2007 | Barnard et al. | |
| 2009/0005859 A1 * | 1/2009 | Keilman | A61B 8/06 623/1.42 |
| 2010/0305666 A1 * | 12/2010 | Lou | A61N 5/0601 607/88 |
| 2012/0148976 A1 | 6/2012 | Brawn | |
| 2012/0199995 A1 | 8/2012 | Pugh et al. | |
| 2015/0202456 A1 | 7/2015 | Andersen et al. | |
| 2015/0246242 A1 * | 9/2015 | Delp | A61N 1/3605 604/20 |
| 2016/0151639 A1 * | 6/2016 | Scharf | A61N 5/0624 607/92 |
| 2016/0344240 A1 | 11/2016 | Yeh et al. | |
| 2017/0216620 A1 * | 8/2017 | Williams | A61N 5/0624 |
| 2017/0312537 A1 | 11/2017 | Mori et al. | |
| 2018/0192952 A1 | 7/2018 | Rogers et al. | |
| 2019/0001149 A1 | 1/2019 | Chabrol et al. | |
| 2019/0240500 A1 | 8/2019 | Lundmark et al. | |
| 2021/0113852 A1 | 4/2021 | Luu et al. | |
| 2022/0296913 A1 | 9/2022 | Luu et al. | |

FOREIGN PATENT DOCUMENTS

| | | | |
|---|---|---|---|
| JP | S62102771 A | 5/1987 | |
| JP | H0394776 A | 4/1991 | |
| JP | H0394777 A | 4/1991 | |
| JP | H0855803 A | 2/1996 | |
| JP | 2000079170 A | 3/2000 | |
| JP | 2008500846 A | 1/2008 | |
| JP | 2011161222 A | 8/2011 | |
| JP | 2016069700 | 5/2016 | |
| JP | 2018502608 | 2/2018 | |
| JP | 2018065058 A | 4/2018 | |
| JP | 2022553301 A | 12/2022 | |
| JP | 2023126647 A | 9/2023 | |
| WO | 9505214 | 2/1995 | |
| WO | WO-03033067 A2 | 4/2003 | |
| WO | 2005099369 | 10/2005 | |
| WO | WO-2012024243 A1 | 2/2012 | |
| WO | WO-2019147619 A1 | 8/2019 | |
| WO | WO-2021081059 A1 | 4/2021 | |

OTHER PUBLICATIONS

"International Application Serial No. PCT/US2020/056609, International Preliminary Report on Patentability dated May 5, 2022", 9 pgs.

"Japanese Application Serial No. 2022-523395, Voluntary Amendment filed Jun. 7, 2022", w/ English Claims, 8 pgs.

"U.S. Appl. No. 17/076,171, Final Office Action dated Jun. 7, 2021", 7 pgs.

"U.S. Appl. No. 17/076,171, Non Final Office Action dated Feb. 19, 2021".

"U.S. Appl. No. 17/076,171, Notice of Allowance dated Jul. 19, 2021", 9 pgs.

"U.S. Appl. No. 17/076,171, Response filed May 4, 2021 to Non Final Office Action dated Feb. 19, 2021", 9 pgs.

"U.S. Appl. No. 17/076,171, Response filed Jul. 6, 2021 to Final Office Action dated Jun. 7, 2021", 7 pgs.

"U.S. Appl. No. 17/076,171, Response filed Dec. 10, 2020 to Restriction Requirement dated Dec. 3, 2020", 8 pgs.

"U.S. Appl. No. 17/076,171, Restriction Requirement dated Dec. 3, 2020", 10 pgs.

"International Application Serial No. PCT/US2020/056609, International Search Report dated Jan. 21, 2021", 2 pgs.

"International Application Serial No. PCT/US2020/056609, Written Opinion dated Jan. 21, 2021", 7 pgs.

U.S. Appl. No. 17/076,171 11,141,602, filed Oct. 21, 2020, Methods and Apparatus for Phototherapy.

"Japanese Application Serial No. 2022-523395, Notification of Reasons for Refusal dated Apr. 21, 2023", w/ English Translation, 17 pgs.

"Canadian Application Serial No. 3,158,283, Examiners Rule 86(2) Report dated Jun. 12, 2023", 4 pgs.

"Japanese Application Serial No. 2022-523395, Response filed Jul. 21, 2023 to Notification of Reasons for Refusal dated Apr. 21, 2023", with English claims, 117 pgs "European Application Serial No. 20878695.4, Extended European Search Report mailed Oct. 30, 2023", 8 pgs.

"Japanese Application Serial No. 2022-523395, Final Notification of Reasons for Rejection mailed Oct. 30, 2023", W English Translation, 10 pgs.

* cited by examiner

METHODS AND APPARATUS FOR PHOTOTHERAPY

CLAIM OF PRIORITY

The present application is a continuation of U.S. patent application Ser. No. 17/076,171 filed on Oct. 21, 2020, which is a non-provisional of, and claims the benefit of U.S. Provisional Patent Application No. 62/923,738 filed on Oct. 21, 2019, now expired; the entire contents of which are incorporated herein by reference.

BACKGROUND

Light delivery as a therapeutic is an integral part of human existence. Light from the sun helps regulate our circadian rhythm and produce crucial Vitamin D in our skin throughout the day. Light is used in the form of therapy to treat conditions of the eyes and skin, or to reduce bilirubin levels to treat newborn jaundice. Light delivery may be used to treat a number of other conditions.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Light delivery as a therapeutic is an integral part of human existence. Light from the sun helps regulate our circadian rhythm and produce crucial Vitamin D in our skin throughout the day. Light is used in the form of therapy to treat conditions of the eyes and skin, or to reduce bilirubin levels to treat newborn jaundice. More recently, light has been seen as a potential source for new treatments paired with photo-activated drugs, leading to new advancements in skin cancer as well as some internal tumors and other conditions.

The main challenge of using light to treat internal diseases is that light does not travel very far into the body. Light is absorbed by the skin and tissue, which limits the penetration depth of visible and near-infrared (NIR) wavelengths to 3 to 5 millimeters. Applying phototherapy to tumors or stimulating neurons to treat movement disorders may require light at 10-25 cm depths, less depth, or even greater depths, and an implantable light source adjacent the target treatment area is the only practical way for light to reach such depths in the human body.

This disclosure describes novel powering, light delivery, and integration aspects of an implantable phototherapy device, system and methods of use. The implant can also be designed to deliver a single treatment and/or integrated with other forms of stimulation and/or therapeutic agents other than light, and in doing so deliver innovative combination therapies. The implant can also be modified to include sensing properties, such as to modulate treatment dosage in response to the patient's physiological state.

Figure 1:
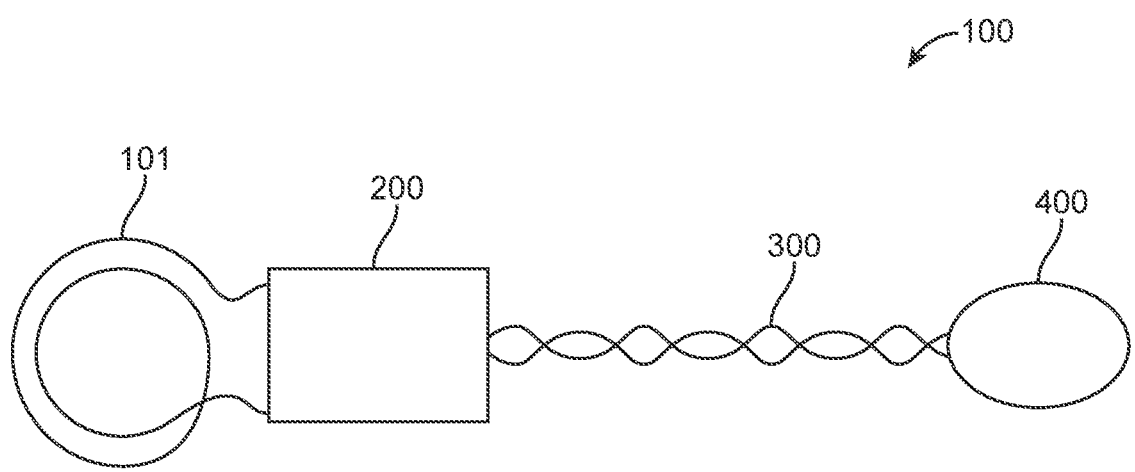
FIG. 1 illustrates a light illumination system.

FIG. 1 shows an example of a light illumination system 100 that may be used to deliver phototherapy inside a patient's body, for example in the treatment of tumors deep in the body, such as glioblastomas in the brain. While the examples disclosed herein are primarily directed to implantation of the device in the brain as a treatment for brain cancer, this is not intended to be limiting and one of skill in the art will appreciate that the device may be implanted in any other part of the body to deliver phototherapy inside the body as part of a treatment for other conditions. Thus, the devices and systems described herein may be surgically implanted in a tumor cavity created by resection of a tumor, or they may be placed in natural body cavities adjacent to diseased areas or in native tissue without surgical modification (e.g. by implantation directly into tissue). In either situation, the light may be used to activate various therapeutic agents that help fight the tumor or provide other therapeutic effects to treat a disease, thereby providing localized therapy. For example, in photodynamic therapy, light may be used to activate a therapeutic agent (also referred to as a photosensitizer) absorbed by cells, which results in the production of reactive oxygen species (ROS) which is toxic to the host cells and leads to cell death such as in the tumor, and this is well reported in the patent and scientific literature. The production of ROS may be quantified by titration methods known in the art. The wavelength of the light must overlap with the activation spectra of the photosensitizer.

The illumination system includes a power receiver element which may include a wireless coil 101 and a housing 200. The system also may include a tether wire 300, and a light source (also referred to as a light or illumination element, or light source) 400.

The power receiver element in this or any example may or may not include any energy storage device (e.g. a battery, a capacitor, or other storage element). If there is no storage device, then therapy is only provided when the external power source is activated. If an energy storage device is included, the device may be turned on as needed and the illumination element is powered by the energy storage device. The wireless coil 101 is configured to receive radiofrequency energy from an external transmitter coil in an external power source and may have one or more turns of conductive wire covered with an insulator. The turns may take any geometry such as circular or helical coils and the coils may be made of any material that is conductive to electromagnetic energy. The wireless coil may optionally be made from a printed circuit board or a flexible printed circuit board with metal or conductive traces in a circular or other coil pattern. The coil is sized for wireless power transmission through tissue, such as through the scalp of a patient at any depth such as a depth of less than about 5 cm, 4 cm, 3 cm, 2 cm, or 1 cm, and the coil is able to tolerate variations in intervening tissue thicknesses. The wireless transmitter and receiver may optionally be capable of bidirectional authentication so that only approved devices can work together and transmit power to the implanted device. Optionally, secure, cryptographic technology may be used to ensure that the device cannot be activated by an unauthorized user or transmitter.

The wireless coil 101 may be electrically and mechanically coupled to an optional housing 200 so that energy captured by the coil 101 is delivered to the housing 200 which contains various electronic components for managing the power and controlling the duty cycle of the light source 400. The electronics in the housing may be mounted on a printed circuit board.

The housing may be any size or shape and may be formed of any number of materials such as titanium or any material that is biocompatible. The wires from the coil 101 or the tether 300 may be coupled to the housing via ceramic feedthroughs. Additional disclosure about the electronic components in the housing 200 is provided later in this specification.

A tether wire 300 is operably coupled to both the housing 200, the electronics in the housing 200, and the light source 400. The tether ensures that the light source 400 remains coupled to the housing and may be formed from any material with appropriate strength for tethering as well as being electrically conductive. The tether wires may be soldered to electronic feedthroughs in the hermetically sealed housing (sometimes also referred to as a "can") that encloses the power source electronics. The tether 300 may be several wires that run linearly between the housing and the lighting element, or the wires may be coiled, helically wrapped, braided, twisted together, or take any configuration, and have adequate length to ensure that the housing can be anchored in one position and the light source may be disposed in a desired location. The tether may include a plurality of electrical wires passing through a multi-lumen tubing resulting in a single filament, or the tether may have more than one filament.

The light source 400 may be a single light source or may include a plurality of light sources. For example, a plurality of light sources may be included in the light source and that are configured to be adjusted to various intensities and may all have the same or different wavelengths of light which may be controlled either together or independently of one another. The wavelength may be selected to maximize photoactivation of a therapeutic agent.

Figure 2:
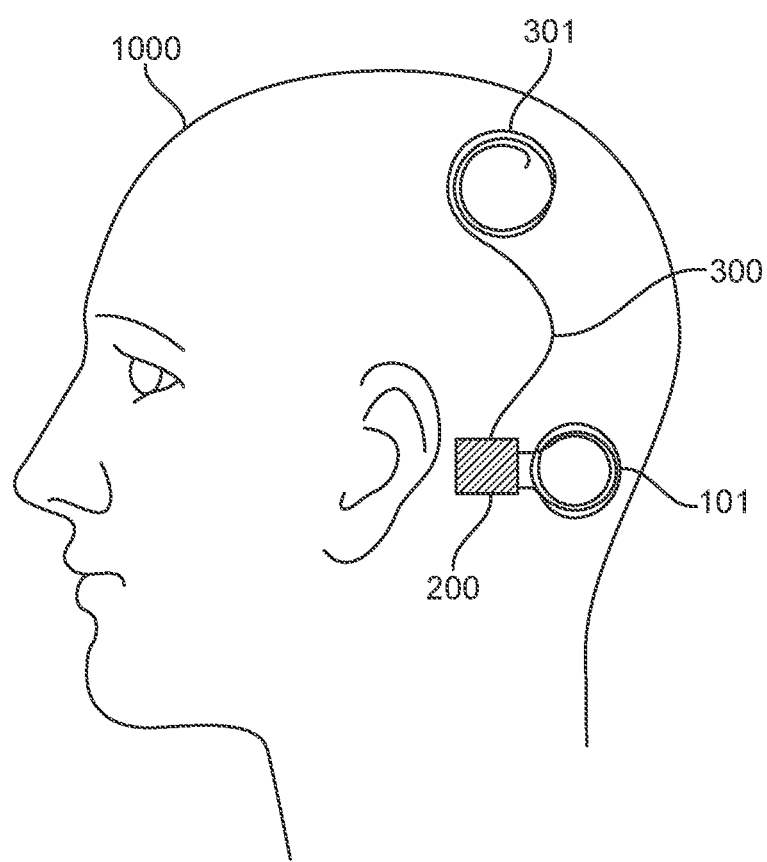
FIG. 2 illustrates a light illumination system coupled to a patient's head.

FIG. 2 shows the phototherapy system of FIG. 1 coupled to a patient's skull 1000. Here, the phototherapy system includes a power receiver element which has a coil 101 for receiving RF energy from an external power source and a housing 200 containing electronic components for controlling the device. A tether 300 operatively couples the housing with the illumination element which is disposed in a tissue cavity in the patient's brain after resection of a tumor. The illumination element is not visible in this view. The tether may be coiled 301 along any portion of its length in order to take up excess slack or to provide a strain relief. In this example, the power receiver element is attached to the patient's skull using techniques known in the art such as with sutures, staples, an adhesive, or with fasteners such as screws so that the power receiver element is disposed under the scalp. The tether is also disposed between the scalp and skull. A burr hole may be drilled through the skull to allow the tether and illumination element to be passed through the skull into the tissue cavity where the illumination element may be attached to the tissue to secure it in a desired position where it will illuminate the target treatment tissue to provide therapy, such as activating a drug which reduces or eliminates tumor cells that may be left over after resection, or that may recur. The burr hole may be the same as the burr hole used to provide the surgeon access during the tumor resection, or it may be a separate burr hole. In this example, the power receiver element may be disposed behind the ear as shown, or the power receiver may be disposed anywhere along the skull.

Optionally, a fastener such as a clip or grommet (not illustrated) may be used to help protect the tether as it passes through the opening in the skull which may have sharp edges. The fastener helps to hold the tether in place so the tether cannot be pulled out and provides cable management to prevent entanglement of the tether. The fastener may be formed from any biocompatible material such as polymers, silicone, metals, etc.

Figure 3:
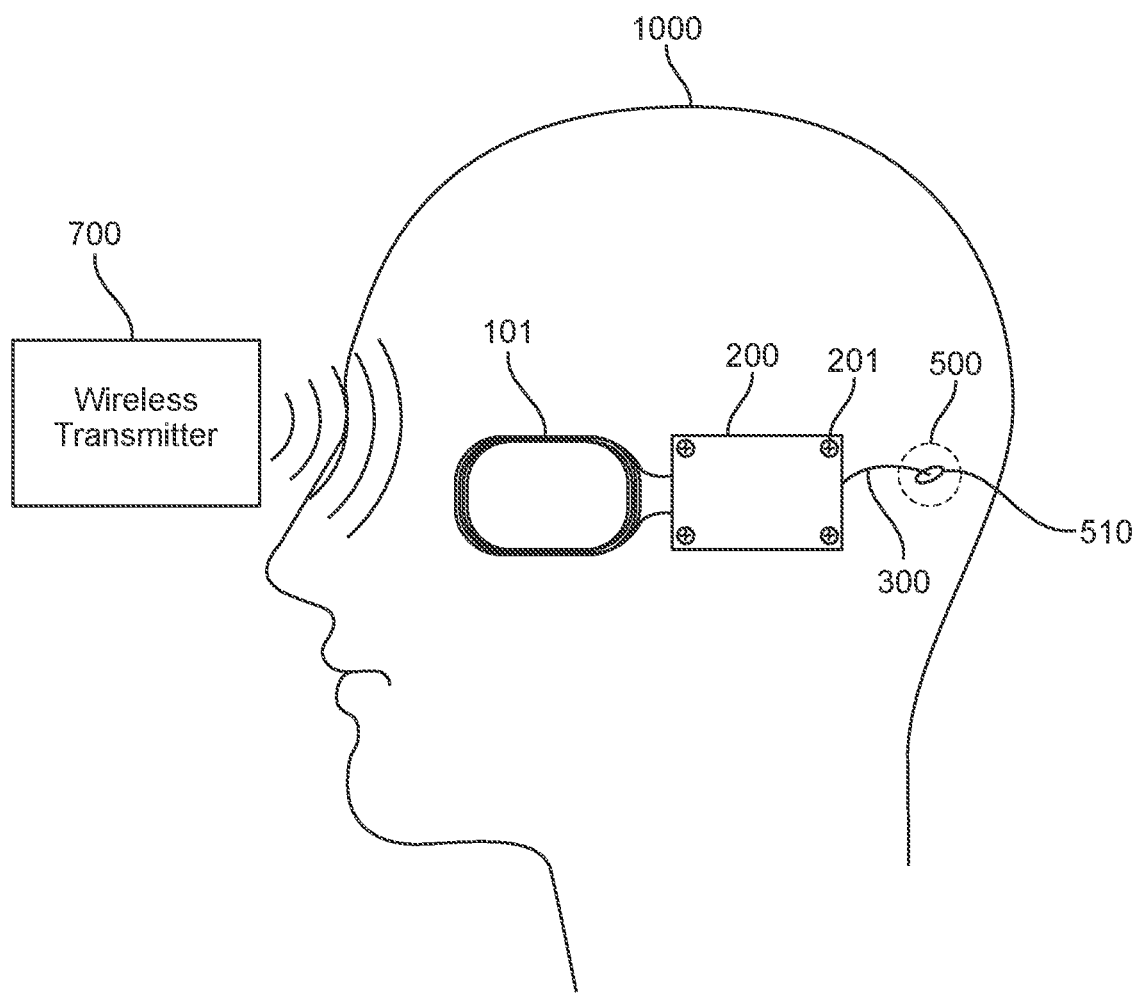
FIG. 3 shows a light illumination system coupled to a patient's head.

FIG. 3 shows show the phototherapy system of FIG. 1 along with an external power source 700 which provides radiofrequency power wirelessly to the phototherapy system. The phototherapy system includes a power receiver element that includes a coil 101 for receiving radiofrequency energy (RF) energy from the power source 700, here a RF wireless transmitter. The power receiver element also includes a housing 200 that contains the electronic components for controlling the phototherapy system. Fasteners 201 such as screws maybe be used to secure the housing to the skull 1000 under the scalp. A tether 300 electrically couples the housing and the electronic components in the housing with the illumination element (not seen) that is disposed in a cavity in the brain tissue formed after the tumor has been resected. The bone plate 500 may be repositioned in the burr hole to help close the skull and a grommet 510 or clip may be used to help secure the tether to the skull and prevent damage to the tether. The tether may be coiled or uncoiled. Here the power receiver element is positioned on a side of the patient's head, about eye level.

Figure 4:
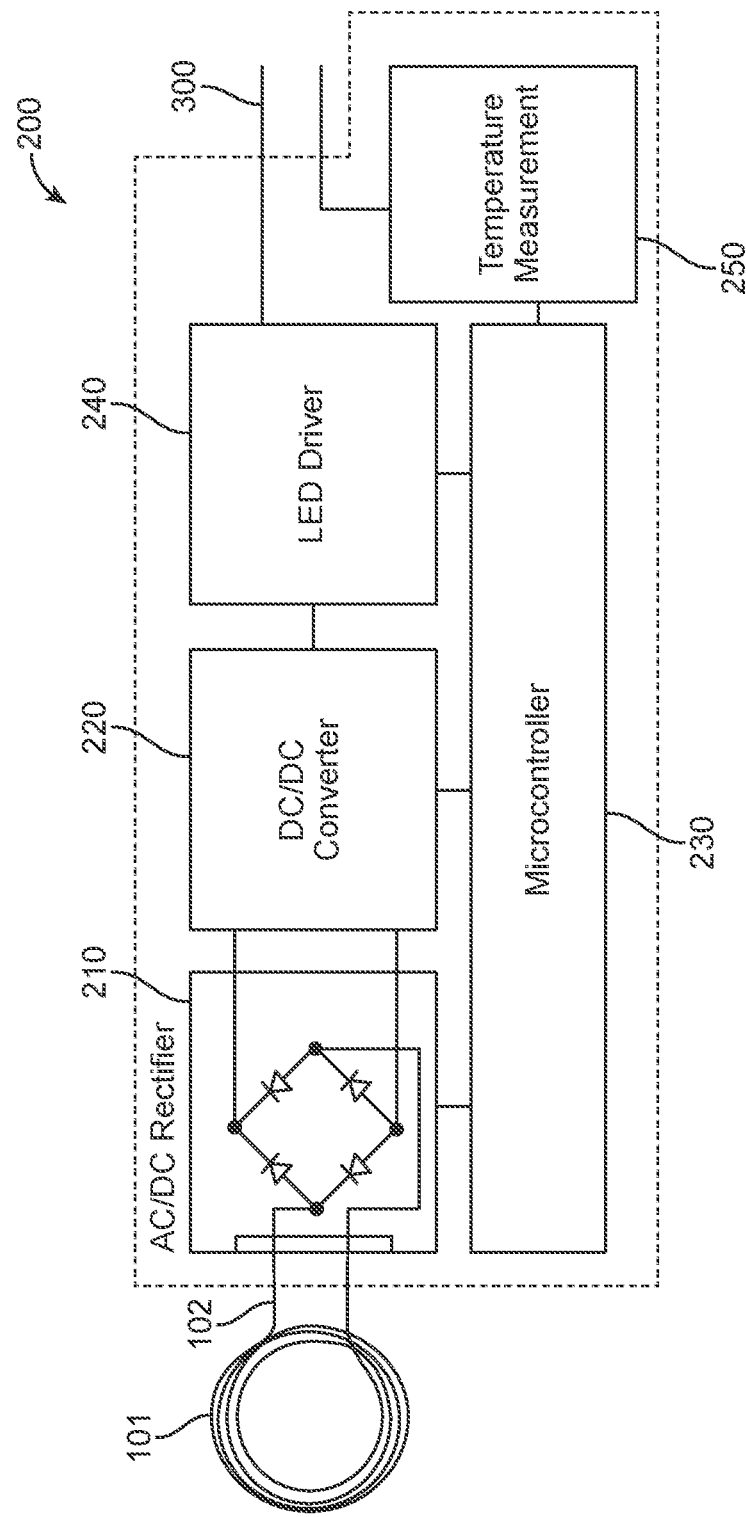
FIG. 4 shows an example of electronic components in a housing.

FIG. 4 illustrates an example of the housing 200 that may be used with any example of phototherapy system disclosed herein. Some of the electronic components which may be disposed in the housing to help control the phototherapy system include a rectifier such as a full wave bridge rectifier 210 comprising four diodes arranged to convert alternating current (AC) received from the coil 101 to direct current (DC). A DC/DC converter 220 may be coupled to the rectifier and converts the power or voltage level from one level to another level and this is operatively coupled to an illumination driver 240 which drives the illumination element (not illustrated) which may be one or more light sources such as light emitting diodes. A microcontroller 230 may also be included in the housing to control the system. An impedance matching network 102 may couple the coil to the rectifier to ensure maximum power transfer and minimize loss. The impedance matching network may include capacitors or may have active electronics to tune the resonance. The housing may also include a temperature measurement component 250 which helps monitor temperature from a sensor disposed at the target treatment site (not shown) thereby ensuring temperature at the light source is not excessive and does not cause tissue damage. The temperature measurement component 250 may also monitor temperature of the receiver electronics to ensure that overheating is avoided. The housing may be formed from any biocompatible material such as titanium and provides a hermetic seal for the electronic components. The housing may serve as a heat dissipation element, or a separate heat dissipation element (not shown) may also be included in the housing. Electrical leads exiting the housing form the tether 300 which is coupled to the illumination source.

Figure 5:
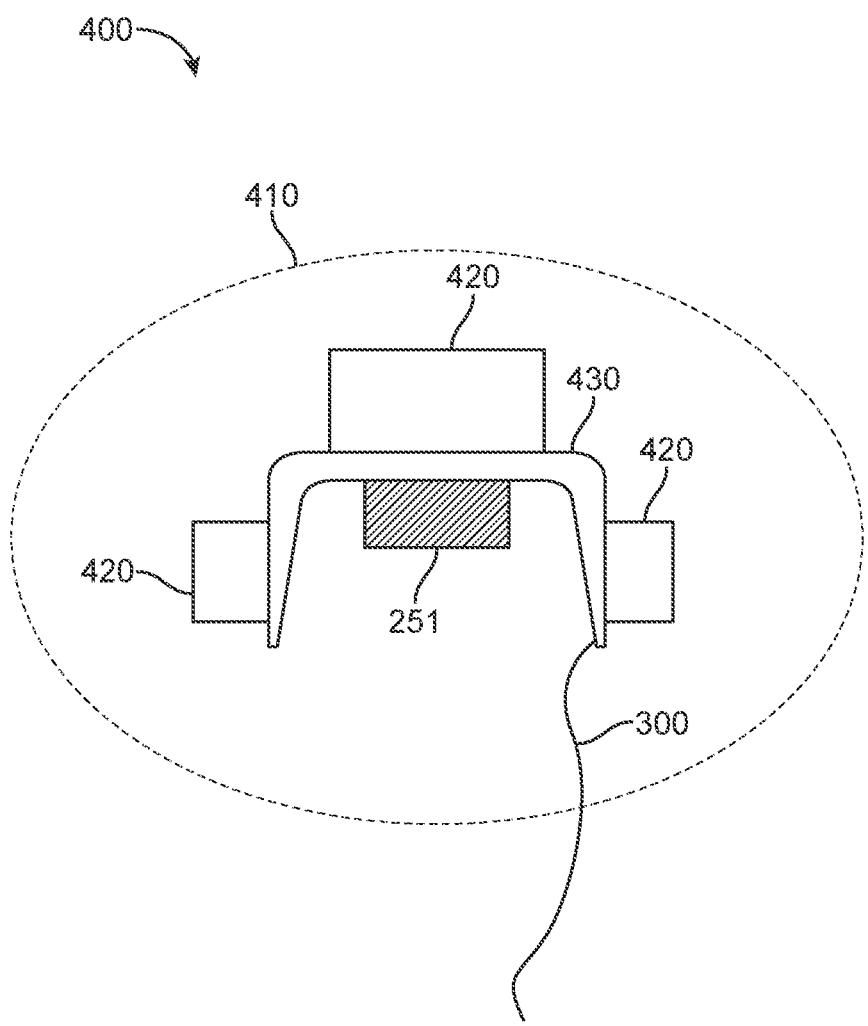
FIG. 5 illustrates an example of an illumination element.

FIG. 5 shows an example of an illumination element 400 that may be coupled to the tether 300 and that may be used in any example of an illumination system. The tether allows power to be delivered from the power receiver element to the illumination element and optionally also electrically couples an optional temperature sensor with the electronics in the housing. The tether also provides a mechanical coupling between the illumination element 400 and the power receiver element so the two remain coupled together. Here, the illumination element 400 includes one or more flexible substrates 430 such as a flexible printed circuit board (PCB) which may be shaped in any desired configuration in order to conform with the target treatment area. Polyimide is one example of a suitable PCB material. The target treatment area may be a cavity in the brain that is created after a tumor is resected therefore the substrate should be formable into a three-dimensional shape. Additionally, the flexible substrate once formed helps support the tissue surrounding the cavity to prevent it from collapsing inward which can prevent some of the tissue from being illuminated. Here, a plurality of illumination elements 420 are coupled to the flexible substrate and the substrate is bent into an upside down square U-shaped configuration (or a staple with two vertical legs and one horizontal bar connecting the legs) so that one illumination element 420 is on each leg of the U-shape, and one illumination element is on the horizontal connector between the legs of the U-shape. This ensures that light emitted from the illumination element will be distributed radially outward and evenly in several different directions to illuminate the target treatment area. The illumination elements 420 may be one or more LEDs that can be controlled independently of one another or controlled together. The LEDs may emit a single wavelength of light or several wavelengths of light and their intensity may also be adjusted as well as the duty cycle of how long they are on and how long they are off. The PCB may include other electronic components that help control the lights and automatically direct power from the tether to each LED successively in a desired cycle. This allows light intensity to be increased or decreased as desired in order to control illumination of different areas of the tumor cavity. As the LEDs cycle, more intense light exposure followed by periods of darkness which may increase the activation of the photosensitizer while giving oxygen in the tissue time to recover between cycles of illumination when the cavity is dark. The light sources and substrate may be encapsulated 410 in a material that protects the device as well as acting as a light guide to help deliver the light to the target treatment area. For example, the encapsulation 410 may be formed from silicone or another translucent material which acts as a light guide to deliver the light, or the encapsulation may help to diffuse the light. The encapsulant may be any shape including a flat planar sheet, square box, rectangular box, round, cylindrical, spherical, ovoid, etc. and is selected to fit the tumor cavity.

An optional temperature sensor 251 such as a thermistor may also be coupled to the flexible substrate in order to allow temperature monitoring at the target treatment area since light may generate heat and overheating is undesirable and may damage tissue. If excessive heat is generated the lights may be turned off. As mentioned above, the illumination elements 420 and temperature sensor 251 may optionally be encapsulated in a material that protects the lights and sensor as well as providing desirable optical properties for delivering light from the illumination element to the target treatment area. For example, the encapsulating material may be optically clear, or it may contain diffusing or reflecting materials (not shown) such as titanium dioxide particles. Then encapsulant may also act as a light guide or waveguide to ensure minimal light loss during transmission. The encapsulant may have a primary layer which is for protection of the lights and to help dissipate heat. An optional secondary layer of encapsulant may be provided that acts as a light guide and facilitates distribution of light to the target treatment area. Examples of multiple layers of encapsulation are disclosed herein, any of which may be used with any example of illumination element.

FIGS. 6A-6D show examples of optical light guide shapes which may be used with any of the illumination elements disclosed herein. The light guides may be integral with the encapsulant that surrounds the light sources, or the light guides may be disposed on top of the encapsulant. The light guide may be formed from the same material as the encapsulating layer or a different material may be used. The optical light guide shapes help distribute light to the target treatment area with minimal loss of light and are shaped to fit into the cavity left behind after tumor resection to ensure that all tissue in the target treatment area is illuminated thereby activating the therapeutic agent. Additionally, the optical light guide may physically or mechanically support the tissue and help prevent the tissue from collapsing which also helps to ensure that all the tissue in the target treatment area is illuminated.

Figure 6A:
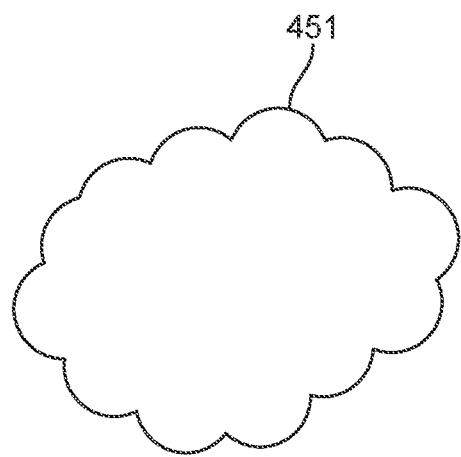
FIG. 6A-6D show examples of optical lightguide shapes.

FIG. 6A shows a cloud shaped optical light guide 451. The cloud shape may include a plurality of lobes that extend radially outward. The light sources and temperature sensor may be disposed in the cloud.

Figure 6C:
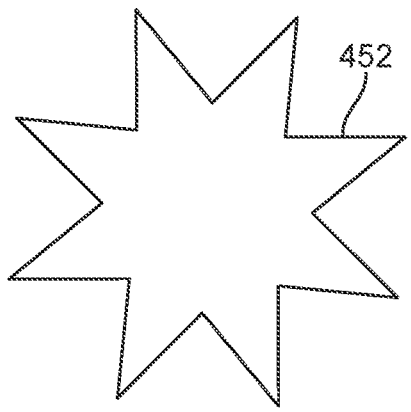
Figure 6B:
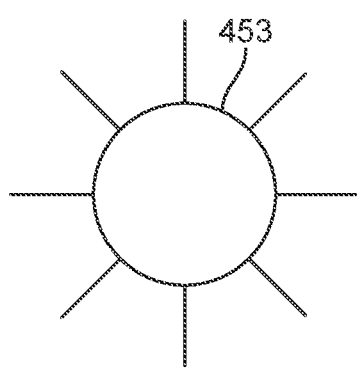

FIG. 6B shows an optical light guide that includes a central spherical ball 453 with spokes extending radially outward. The spokes may be linear spokes or take any other form and may help anchor the optical light guide in the tissue as well as supporting the tissue and directly light to the target treatment area. The light sources and temperature sensor may be disposed in the optical light guide.

FIG. 6C shows a star shaped polygonal optical light guide 452. The star includes a plurality of arms that extend radially outward and each arm may taper radially outward and terminate in a narrow tip. The light sources and temperature sensor may be disposed in the star.

Figure 6D:
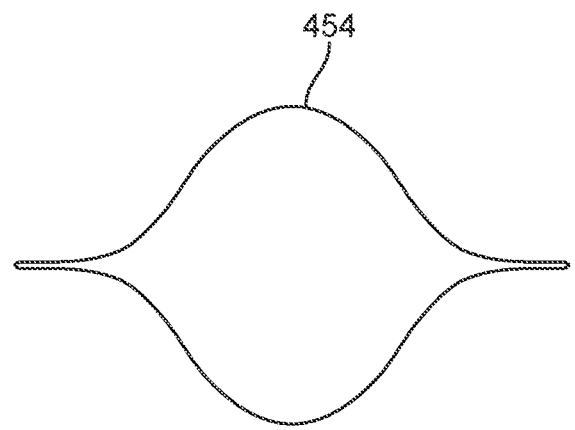

FIG. 6D shows an eye shaped optical light guide 454. The optical light guide may have a wide arcuate middle portion with opposite sides tapering to a narrower portion. The light sources and temperature sensor may be disposed in the optical light guide.

Figure 7:
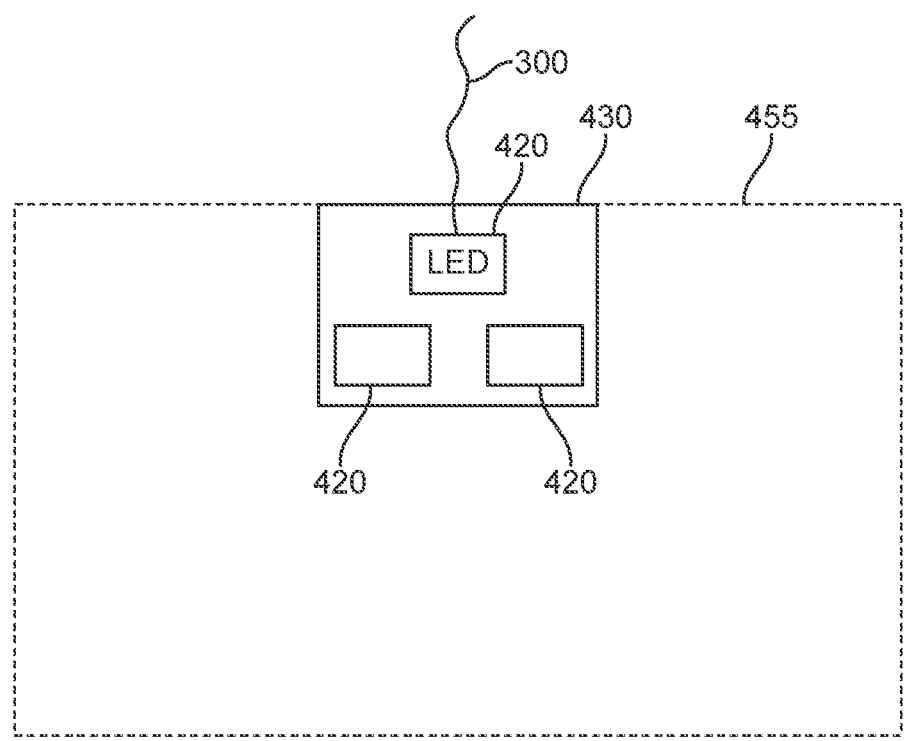
FIG. 7 shows an example of an illumination element disposed on a customizable substrate.

FIG. 7 shows an example of an illumination element having a plurality of light sources, here LEDs 420 disposed on a substrate 430 such as a flexible PCB. The illumination element is coupled to tether 300 so that it may receive power from the power receiver element and the optional temperature sensor (not shown) may be operatively coupled with the electronic components in the housing. The illumination element may be coupled to a flat, planar sheet of material or wallpaper 455 which is formed from an optical material that may serve as a light guide to help distribute light to the target treatment area. The wallpaper may also be referred to as a conformal tensile cavity papering (CTCP) capsule. The flat planar material may be flexed and trimmed/cut to size to conform to the target treatment area and secured to the target treatment area. The entire flat planar material may be trimmable or only certain sections may be trimmable. Regions that should not be trimmed are clearly marked (e.g. adjacent the LEDs). The flat planar material may then be coupled to tissue in the cavity left after tumor resection such as with adhesive, sutures, friction fit, or other techniques known in the art. If adhesive is used, light such as ultraviolet light (UV) may be introduced into the wallpaper and distributed by the wallpaper to the target treatment area to help cure the adhesive, such as cyanoacrylate. The light may be provided by an external light source as will be discussed below.

The wallpaper may be desirable because surgical cavity dynamics post-resection of brain metastases and its implications are known to be a challenge for postoperative radiosurgery in glioblastoma multiforme (GBM) patients. Patients with symptomatic brain metastases are commonly treated with a surgical resection procedure followed by post-operative stereotactic radiosurgery to the surgical cavity for improved local control. Based on numerous brain metastasis expert panels, there is presently no clear consensus on timing of radiation therapy simulations or start dates for these patients. As an illustrative example of challenges faced today, some have opined that there appears to be a theoretical advantage of delayed radiation therapy (4-6 weeks post-op) in response to known surgical cavity collapse, which can thereby decrease target volumes.

Numerous studies exist demonstrating retrospectively assessed surgical cavity changes in patients treated with surgery and post-operative radiation therapy. This cohort's rate of substantial cavity collapse (>2 cm^3) at an average of 24 days postop appears to be in a range between 21-31%. Therefore, some caregivers have concluded that delaying radiation therapy more than two weeks after surgery does not provide a benefit of smaller target volumes. What appears to be clear, is that a significant subset of surgical cavities substantially changes in volume during the period including 3-4 weeks after surgery for a range of reasons including edema control, healing, fibrosis, etc. This has been evaluated to lend an opportunity to decrease treatment volumes by delaying post-operative radiation.

However, treatment delays will have a profound impact in these at-risk patients. In view of known cavity dynamics and cavity collapse, there remains a need to maximize surgical cavity margin light coverage that endures throughout the treatment cycle. The combination of a light source embedded in a CTCP capsule ensures that cavity margin surfaces do not otherwise escape illumination.

Such CTCP capsules may comprise a multi-material matrix that will be used to paper the interior margin of the resected cavity with light. The multi-material matrix includes various materials each having specific properties to maximize the conformal papering effect and, in some instances, to function as a waveguide. The base of the matrix may be a flexible biocompatible material that evenly conforms to the cavity margin shape but does not impede light transmission or fluence. This matrix functions as a scaffold for various standard or bespoke elements including spans of higher tensile strength materials to maximize the expansive effect of the CTCP capsule. Such expansive properties will counteract the tendency of the cavity to collapse, thus ensuring even, consistent, and personalized distribution of photoactivation and light steering. In some instances, the scaffolding function of the base matrix is not limited solely to elements to counteract cavity collapse. In some cases, the multi-material matrix may include elements that scaffold or anchor the light element itself to optimize placement of the various light components and system performance. Such capsules may be personalized. In some examples, the higher tensile span(s) functions as one or more staves. Each stave may be individually controlled to optimize papering. A multi-material matrix may be molded or impregnated with optimized polymer materials. In some instances, the higher tensile strength materials may be embedded in the base of the matrix or protruding therefrom in one or more spans of cavity distending materials. In some instances, the cavity distending materials may or may not anchor or suspend one or more light elements or a light plurality system. Such customization may happen at the point of implantation or work as a modular surgical kit. Such instances may include various multi-material matrices of various shapes, sizes, and configurations. Some CTCP capsules may include one or more radiological markers to aid visualization employing for example, CT and/or MR scans. Such approaches will aid capsule distinction from surrounding tissue, tumor tissue and will allow determination of migration or detachment of the wallpaper and/or illumination elements.

As surgical cavities are known to collapse or shrink, some resection cavities can also have bends and difficult to reach pockets. Such bespoke CTCP capsules may be personalized to combat such challenging cavity conditions and dynamics. Various adhesives, gels, fibrous meshes, and waveguides may also be employed to optimize CTCP capsules. The light source may be embedded into the CTCP. The CTCP material may be over-molded onto the LEDs and printed circuit board. The capsule may be closed, partially enclosed, a modular combination of various capsule elements, and/or may contain one or more pre-configured apertures.

The multi-material matrix may be a plurality of different materials and/or a combination of one or more material thicknesses. The multi-material matrix may be plurality of different materials configured to be expandable to function as an implantable balloon as will be described in more detail below. The CTCP papering kit may comprise a pre-configured assembly of various components designed to allow a caregiver to optimize the CTCP capsule according to patient needs.

Figure 8:
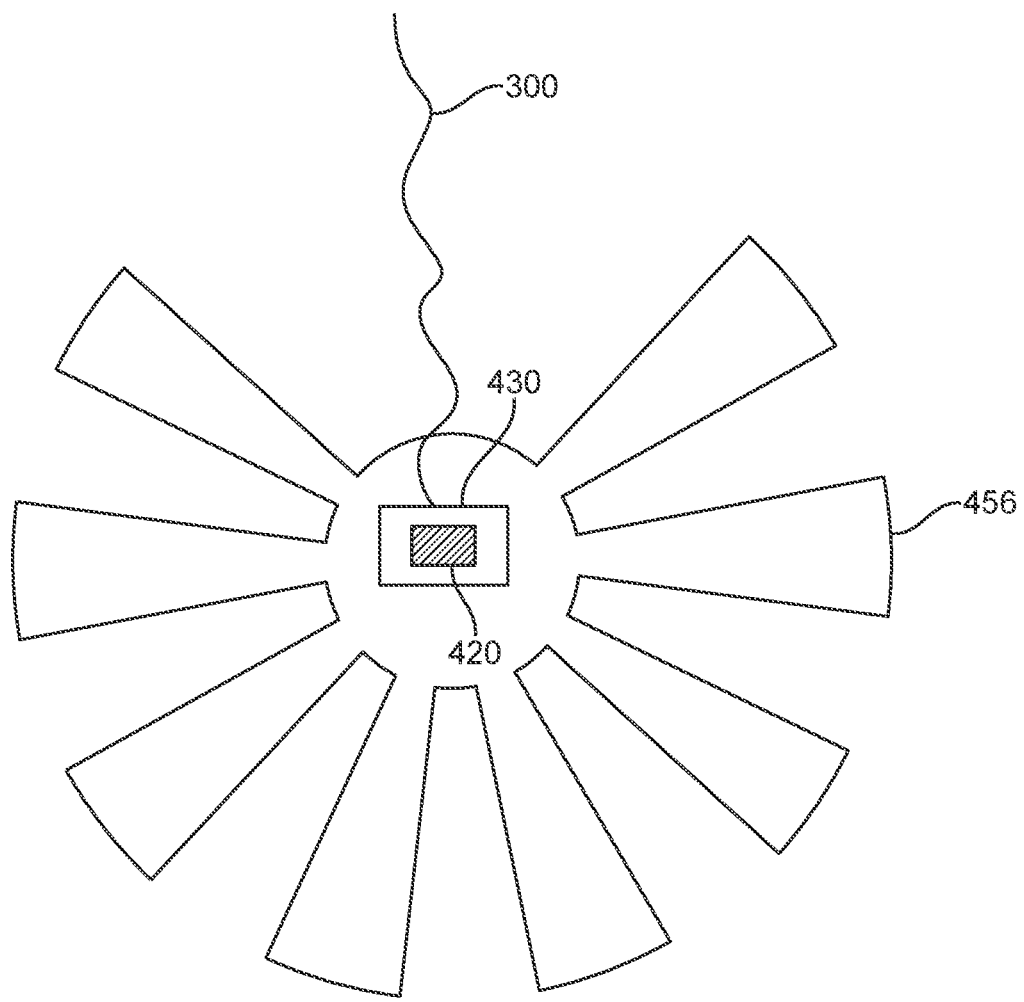
FIG. 8 shows another example of an optical lightguide shape.

FIG. 8 shows another example of a light guide that may be integral with or coupled to an illumination element. Here the illumination element includes one or more light sources 420 such as an LED that are mounted to a flexible or rigid PCB substrate 430. The LEDs are powered via tether 300. The light guide 456 may include a spherical central section with a plurality of spokes radially extending outward, or the light guide 456 may include a flat planar round central section with a plurality of planar spoke extending radially outward. The spokes are formed from an optical material that helps deliver light into the target treatment area with minimal light loss and the spokes also help support tissue in the cavity formed after resection of a tumor, thereby preventing the cavity from collapsing. This helps ensure illumination of the target treatment area. The spokes may be any shape including flat planar rectangular arms, round cylindrical arms, or any other shape.

FIGS. 9A-9D show examples of customized light guides that may be coupled to an illumination element.

Figure 9A:
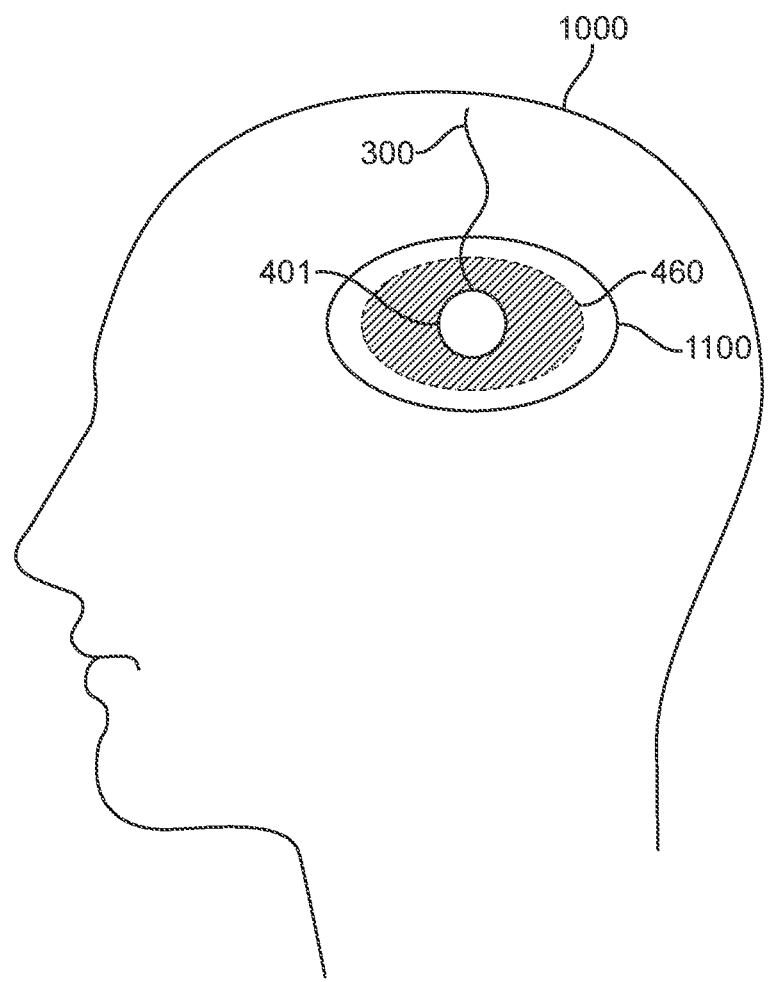
FIGS. 9A-9D show examples of customized light guides that may be coupled to an illumination element.

In FIG. 9A a tether 300 delivers power to a light source encapsulated in a standard shape 401 such as a sphere or a square. The light source is implanted in a cavity 1100 formed after resection of a tumor from the brain in the skull 1000 of a patient. In some situations it may be beneficial to provide an additional light guide element which can be customized to any shape and easily coupled to the encapsulation in order to help support the tissue in the cavity 1100 and to facilitate delivery of light to the target treatment area. In FIG. 9A, and outer light guide 460 that is customized to fit the cavity is coupled to the illumination element, forming an outer ovoid shaped light guide. The outer light guide may be snapped into engagement, adhesively bonded or otherwise coupled to the inner, primary light element.

Figure 9B:
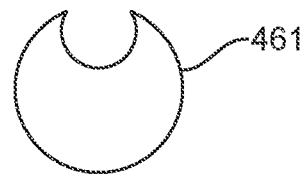
Figure 9C:
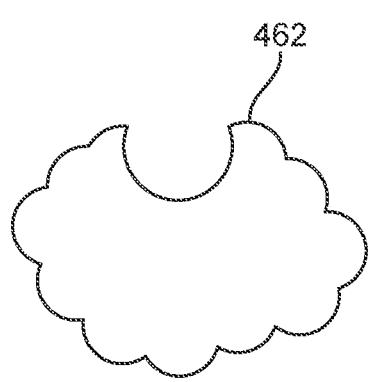
Figure 9D:
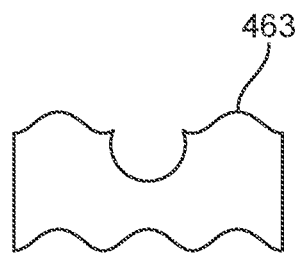

FIGS. 9B-9D show examples of light guides which may be snapped onto, bonded to, or otherwise coupled to the light element.

In FIG. 9B a spherical light guide 461 has a smaller hemispherically shaped recessed area sized to receive the light element. The light element is inserted into the recessed area and then adhesively bonded or snapped in position. In this example the light element is coupled to the light guide 461 off center, however the light element may also be disposed in the center of the spherical light guide.

FIG. 9C shows a cloud shaped light guide 462 having a hemispherically recessed area sized to receive the light element. The light element is inserted into the recessed area and then adhesively bonded or snapped in position. The cloud shaped light guide may include a plurality of lobes that extend radially outward.

FIG. 9D shows a rectangular shaped light guide 463 having linear sides and an arcuate or scalloped top and bottom. The light guide includes a hemispherically shaped recessed area sized to receive the light element. The light element is inserted into the recessed area and then adhesively bonded or snapped in position.

One of skill in the art will appreciate that the examples in FIGS. 9A-9D are not intended to be limiting and that any shape of a light guide may be coupled to the illumination element in order to support the tissue in the tumor cavity and to ensure that light is delivered to the target treatment area.

Figure 10:
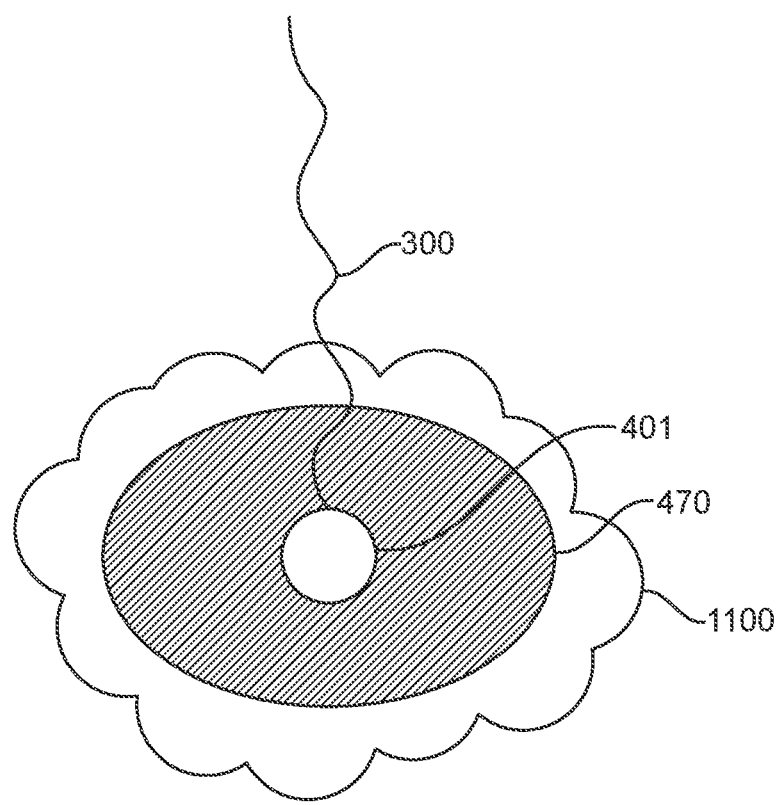
FIG. 10 shows another example of an illumination element.

FIG. 10 shows another example of an illumination element that may be used to conform with the tumor cavity 1100 after a tumor has been resected. Here, an illumination element with encapsulation 401 having any of the configurations described herein is coupled to and powered by power from tether 300. The illumination element in encapsulation 401 may include one or more light sources coupled to a substrate such as a flexible or rigid PCB. The illumination element is coupled to an expandable member 470 such as a balloon instead of the solid encapsulants previously described above. The expandable member is compliant and therefore when it is radially expanded, it will conform to the walls of the tumor cavity and provide uniform support thereby helping to ensure that the target treatment area is illuminated with light. Additionally, the radially expandable member may be adjusted either by further expansion or by collapsing it in order to accommodate changes in the tumor cavity. The expandable member may be expanded with a fluid such as a liquid or a gas. Contrast material may also be used so that the balloon may be visualized with radiographic imaging.

Figure 11:
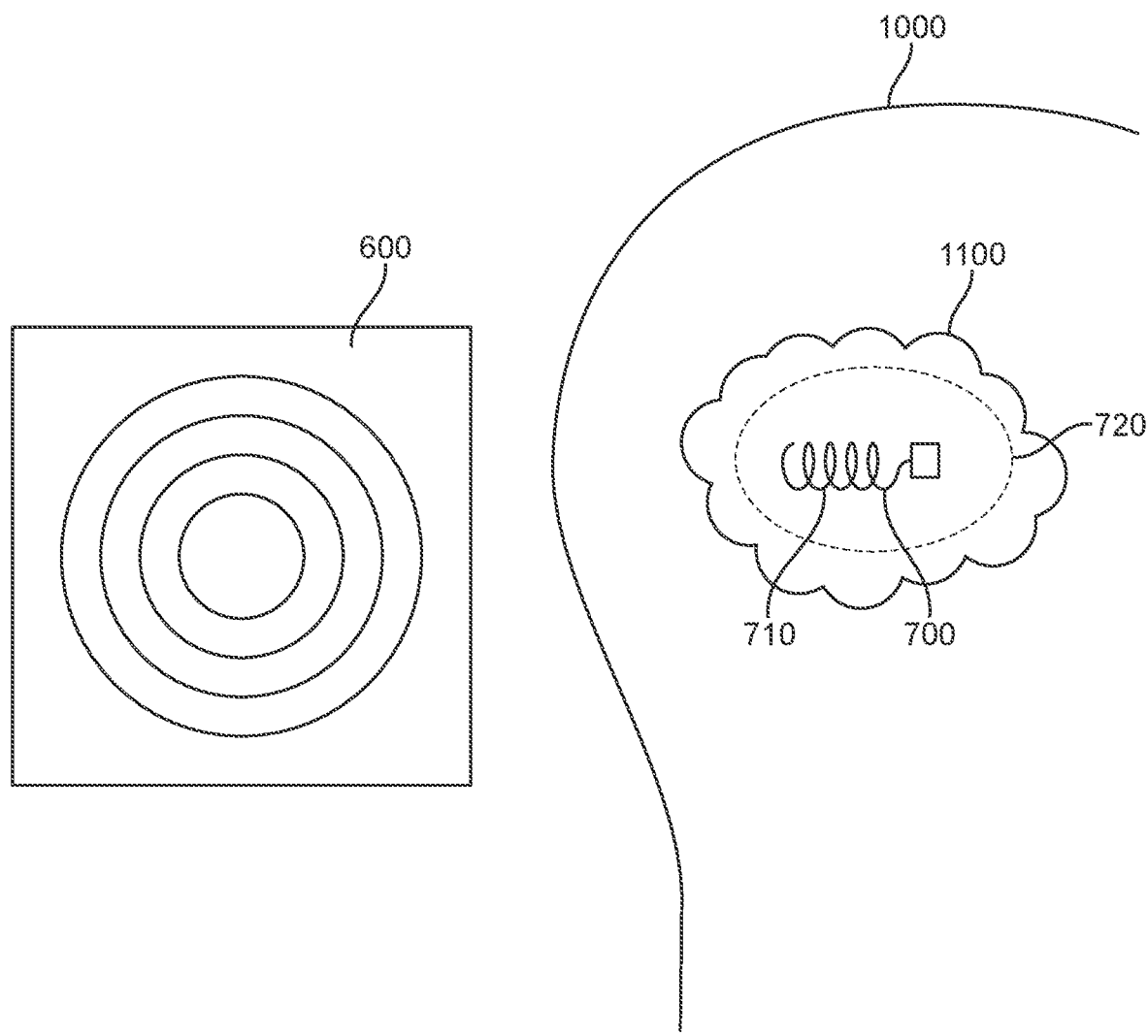
FIG. 11 illustrates the use of planar immersion lens.

FIG. 11 illustrates the use of planar immersion lens 600 that may be disposed on a substrate. The planar immersion lens 600 may be disposed between the external power source (not illustrated) and the power receiver element 700 in the illumination system and helps focus energy onto the receiver for efficient transmission of energy. The substrate may be ridged or flexible and may be disposed adjacent the skull 1000 or attached to the skull 1000 and near the power receiver element. Here, the illumination system may be any of the examples disclosed herein and includes a wireless receiver 700 that is either disposed in the tumor cavity after the tumor has been resection or attached to the skull 1000. The wireless receiver 700 includes an antenna coil 710 for receiving the energy from the external energy source and that is focused onto the coil by the immersion lens. An illumination element which may include one or more light sources such as LEDs are powered by power delivered to the coil. The light sources may be encapsulated in an encapsulant 720 which helps diffuse the light and also helps to hold the implant in position in the tumor cavity 1100. Any of the encapsulants and light guides disclosed herein may also be used with this example of illumination system.

Figure 12:
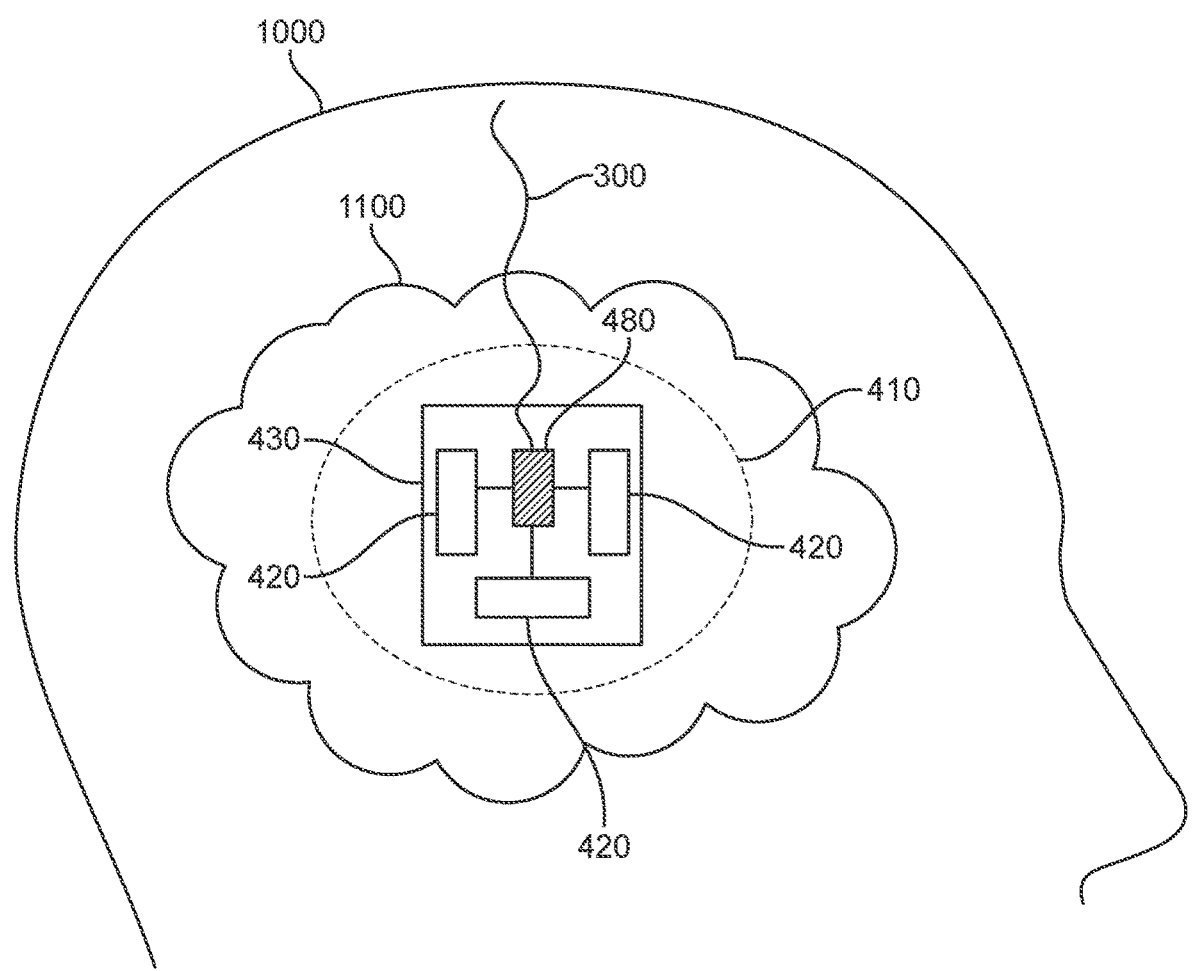
FIG. 12 illustrates the use of multiple light sources in an illumination system.

FIG. 12 illustrates the use of multiple light sources in an illumination system. Here, the illumination element includes multiple light sources 420 that are oriented to provide directional light output. In this example, three light sources 420 such as LEDs are oriented, so light is emitted radially outward and in a different direction relative to an adjacent light source. Here, light is emitted in the 3:00 o'clock direction, 6:00 o'clock direction, and 9:00 o'clock direction. Tether 300 delivers power to the light sources. The illumination element is disposed in a tumor cavity 1100 formed after resection of a tumor from the brain in a patient's skull 1000. The lights are independently controllable to steer the light and also to independently adjust light intensity and on/off timing. Some electronics 480 may be disposed on the substrate 430 which holds the lights 420. The substrate 430 may be a printed circuit board. The illumination element may be encapsulated 410 in an optical material which facilitates light delivery such as by helping to diffuse the light or transmit the light efficiently as well as providing a protective covering to the light sources. Any of the encapsulants or light guides described herein may be used as the encapsulant. Having multiple lights allows varying light therapies to be provided.

Figure 13:
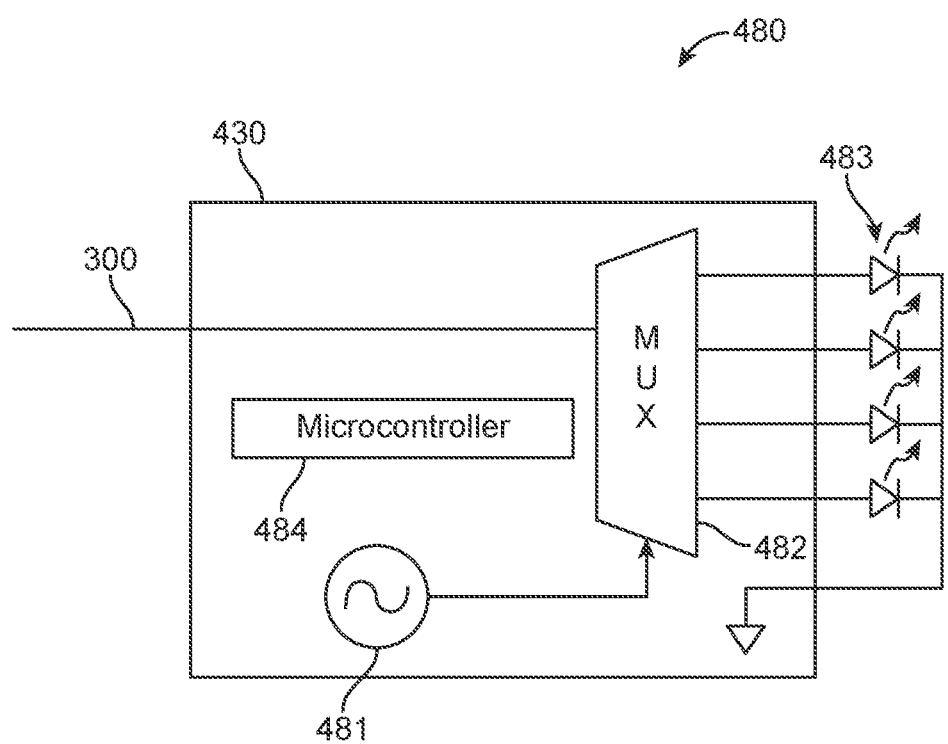
FIG. 13 shows an example of a light source control.

FIG. 13 shows an example of a light source control 480 that may be used with any example of illumination system described herein such as in FIG. 12. The light source control 480 controls illumination of the target tissue when multiple light sources are used and allows independent control of the light sources. The control 480 includes an oscillator 481 and multiplexer 482 that cycles through each of the four LEDs 483 shown in FIG. 13 on a desired switching frequency. In an alternative example, a microcontroller 484 may control the oscillator 481 and the multiplexer 482. A tether 300 connects the control with the power receiver element. The electrical components may be mounted on a PCB 430. The control 480 may also be in the housing instead of the illumination element.

Figure 14:
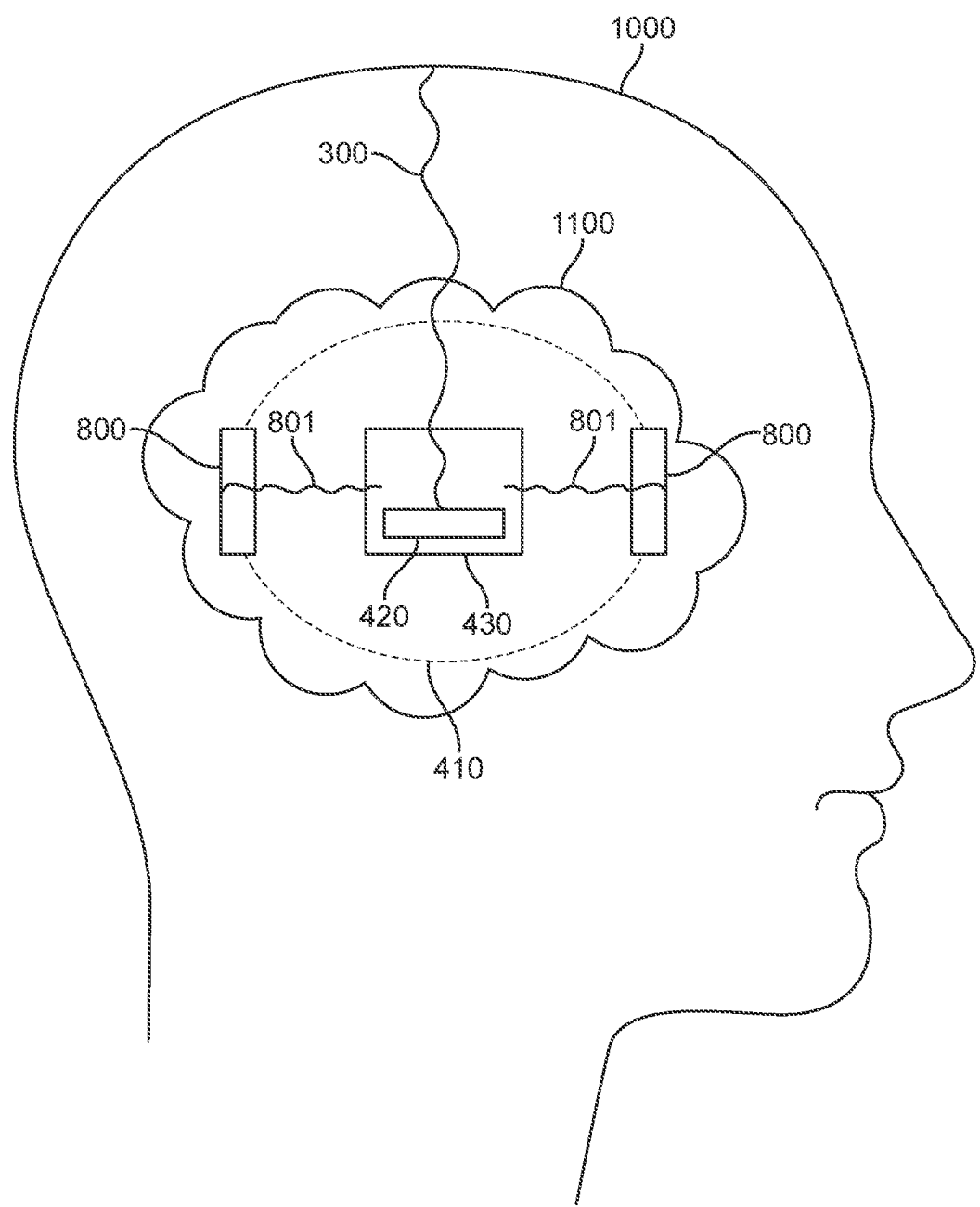
FIG. 14 illustrates an example of an illumination system that may also include electrical stimulation to the target treatment area.

FIG. 14 illustrates an example of an illumination system that may also include electrical stimulation of the target treatment area. Here, after a tumor is resected from the brain in a patient's skull 1000, an illumination system is disposed in the tumor cavity 1100. The illumination system may be any of the systems disclosed herein and may include a tether 300 for providing power to the illumination element 420 which may have one or more light sources coupled to a substrate such as a PCB 430. The lights and substrate may be encapsulated 410 in a material that protects the device as well as facilitates delivery of the light to the target treatment area such as by serving as a light guide or by diffusing the light. The encapsulation may be any of the encapsulation examples or light guides disclosed herein and also may help secure the device into the tumor cavity. Extending from the PCB are conductors 801 which are attached to electrodes 800 that are exposed to the sides of the illumination element and can provide electrical stimulation (deep brain stimulation) to the target treatment area either by direct contact with the brain tissue or by conduction through interstitial fluid in the resected cavity. Thus, phototherapy and electrical stimulation may be provided concurrently. An illumination system such as that of FIG. 14 may be used to provide deep brain stimulation in patients with neurodegenerative diseases such as Parkinson's disease, amyotrophic lateral sclerosis (ALS), Alzheimer's disease, or any other condition where neurostimulation is beneficial. The stimulation may be provided alone or in combination with phototherapy where light may be used to treat a disease such as by activating a photosensitizer including but not limited to brain cancers. Electrodes for tissue stimulation, whether in the brain or elsewhere in the body may be used with any of the examples of phototherapy systems described herein. Additionally, the phototherapy system with electrodes are not limited to implantation in a tumor cavity formed after tumor resection. The phototherapy system may be placed in any tissue where phototherapy and/or electrical stimulation are to be delivered to treat any disease or condition.

Figure 15A:
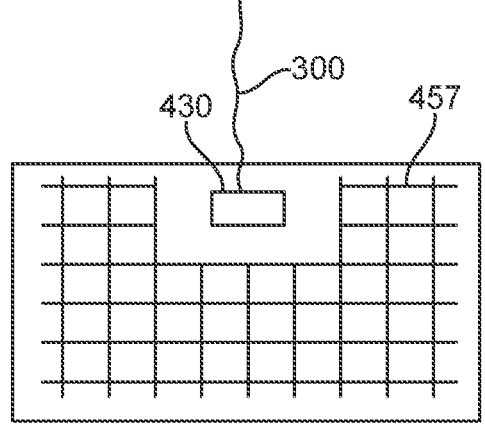
FIG. 15A illustrates an example of a reinforced substrate.

FIG. 15A shows an example of a reinforced substrate that may be used with any of the examples of light and/or electrical stimulating systems disclosed herein. For any substrate used in these examples, e.g. the substrate on which the light sources are mounted, or the light guide substrates, it may be advantageous to use a substrate that has reinforcing in the substrate to either provide a stiffer substrate or a substrate that can be bent, flexed or otherwise shaped to fit the target treatment region and retain that shape. Here, the substrate is similar to substrate 455 in FIG. 7 and is a flat planar substrate which may be trimmed to a desired size and shape to fit the target treatment area. The substrate may be formed from a material that has stiffening features, or stiffening features may be built into the substrate. For example, here a two-dimensional grid of ribs 457 may be formed into the substrate to provide desirable stiffening characteristics. This helps the substrate maintain its shape once disposed in the tumor cavity created after resection of the tumor. The illumination element 430 (which may be any of those disclosed herein) may be positioned anywhere along the substrate and a tether 300 is coupled to the illumination element 430 for supply of power. The stiffening features may be formed from a different material (e.g. a different polymer) having different mechanical properties (e.g. Young's modulus of elasticity, durometer, etc.) compared to the base substrate.

Figure 15B:
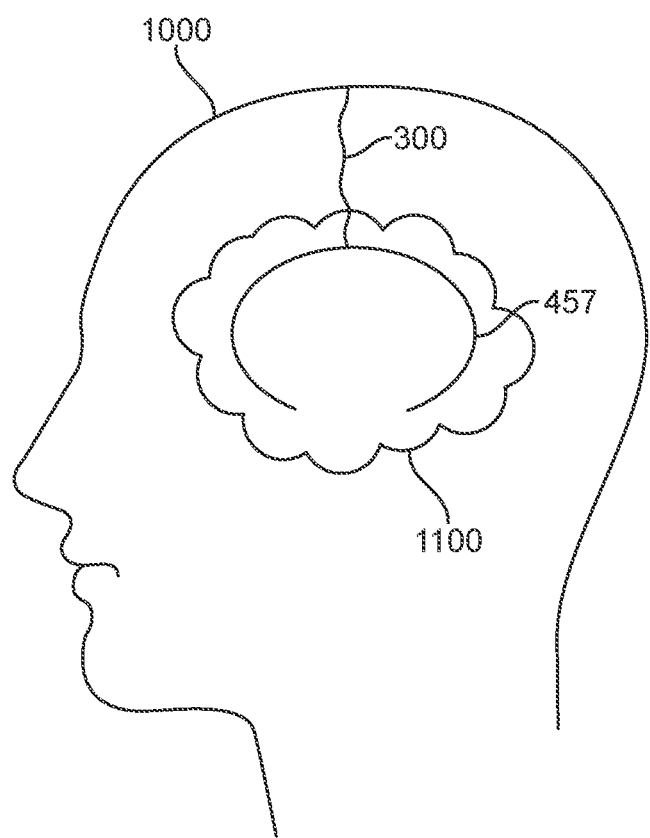
FIG. 15B shows the reinforced substrate of FIG. 15A disposed in a tumor cavity.

FIG. 15B shows the device of FIG. 15A with stiffening features in the substrate implanted in a tumor cavity 1100 in a skull 1000. The tether 300 provides power to the illumination element (not shown in this view) which is coupled to the substrate with stiffening or reinforcing members. The substrate is formed into a partially closed loop if two dimensional, or a partially closed spheroid if three dimensional, to support and conform to the tissue and illuminate the tissue. The substrate serves as a light guide to help illuminate the target treatment area.

Figure 16:
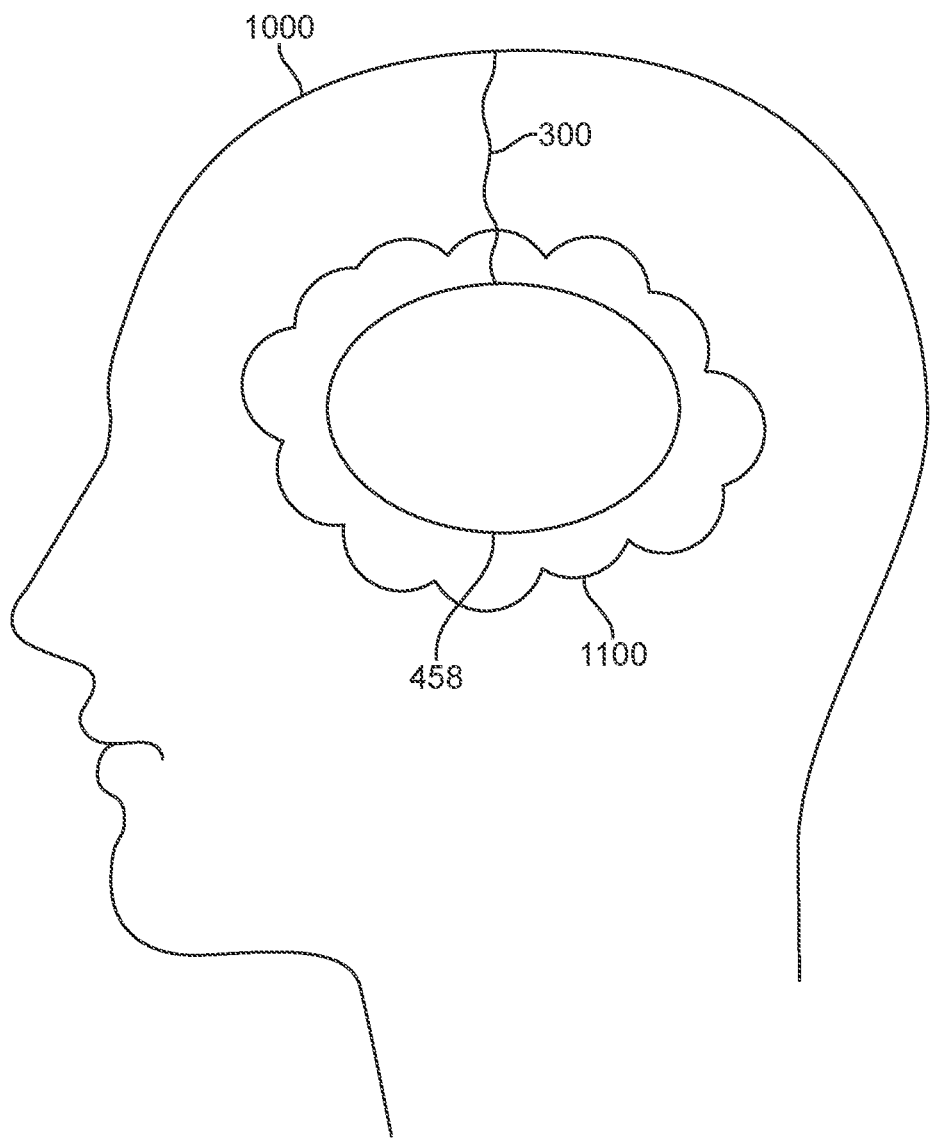
FIG. 16 shows another example of a reinforced substrate.

FIG. 16 shows another example of a reinforced substrate such as the example of FIG. 15A formed into a closed loop if two dimensional, or a closed spheroid if three dimensional. Here, power is delivered via tether 300 to the illumination element (not shown, and which may be any illumination element disclosed herein) which is disposed on the reinforced substrate 458 in tumor cavity 1100 in skull 1000. The reinforced substrate may be the same as shown in FIG. 15A or different, and the ends may remain apposed with one another in a closed configuration due to the reinforcements in the substrate which maintain the desired shape, or due to use of adhesives. This helps maintain the substrate in a desired configuration which supports the tumor cavity to ensure proper illumination of the target treatment area.

Figure 17:
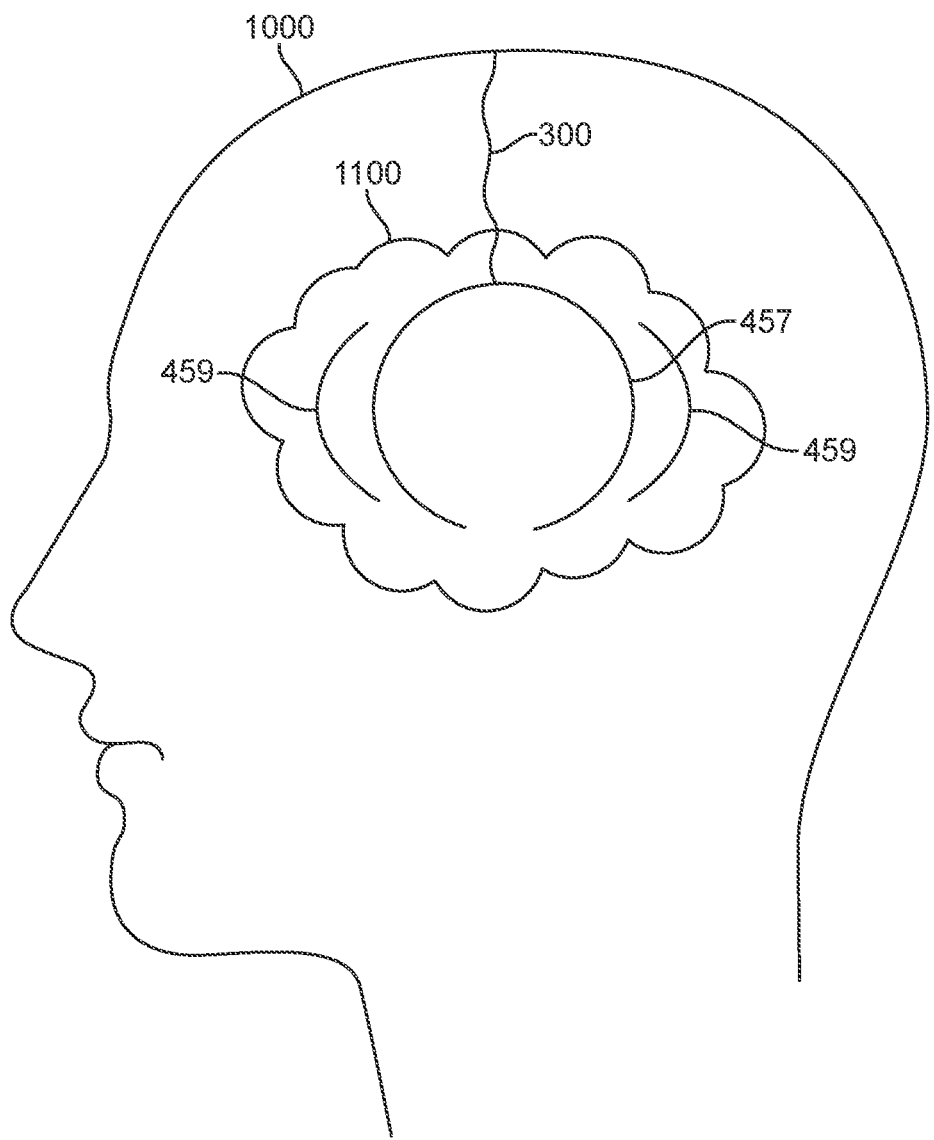
FIG. 17 illustrates the use of additional support elements in a tumor cavity.

FIG. 17 illustrates the use of additional support elements in a tumor cavity 1100 in the skull 1000 of a patient. The wallpaper substrate concept described in FIGS. 7, 15A-15B, and 16 may be used with additional support elements disposed in the tumor cavity to help support the tissue in the target treatment area and also to help distribute light to the target treatment area. Here, a tether 300 provides power to an illumination element which may be any of those disclosed herein. The illumination element may be encapsulated in a material, and the combination of the illumination element and encapsulant may be coupled to a flat planar substrate 457 that is shapeable and trimmable to fit in the tumor cavity. The flat planar substrate 457 may be any of those described herein and may be optically transparent to ensure the light passes through it. Here, the wallpaper is formed into a partially closed loop if two dimensional, or a partial sphere if three dimensional. In some situations it may be beneficial to provide additional support elements 459 that help support tissue in the tumor cavity and prevents collapse, and also that may be formed of optical material thereby forming a light guide that helps distribute the light to the target treatment area. The support elements maybe thin planar sheets of material that are trimmed and shaped to fit into the tumor cavity or they may be prefabricated into various desired shapes. The support elements may then be secured to tissue in the tumor cavity using techniques known in the art such as with sutures, adhesives or other techniques. The additional support elements may also act as a spacer between tissue and the illumination element, or an optical instrument to help deliver the light to the tissue.

Figure 18:
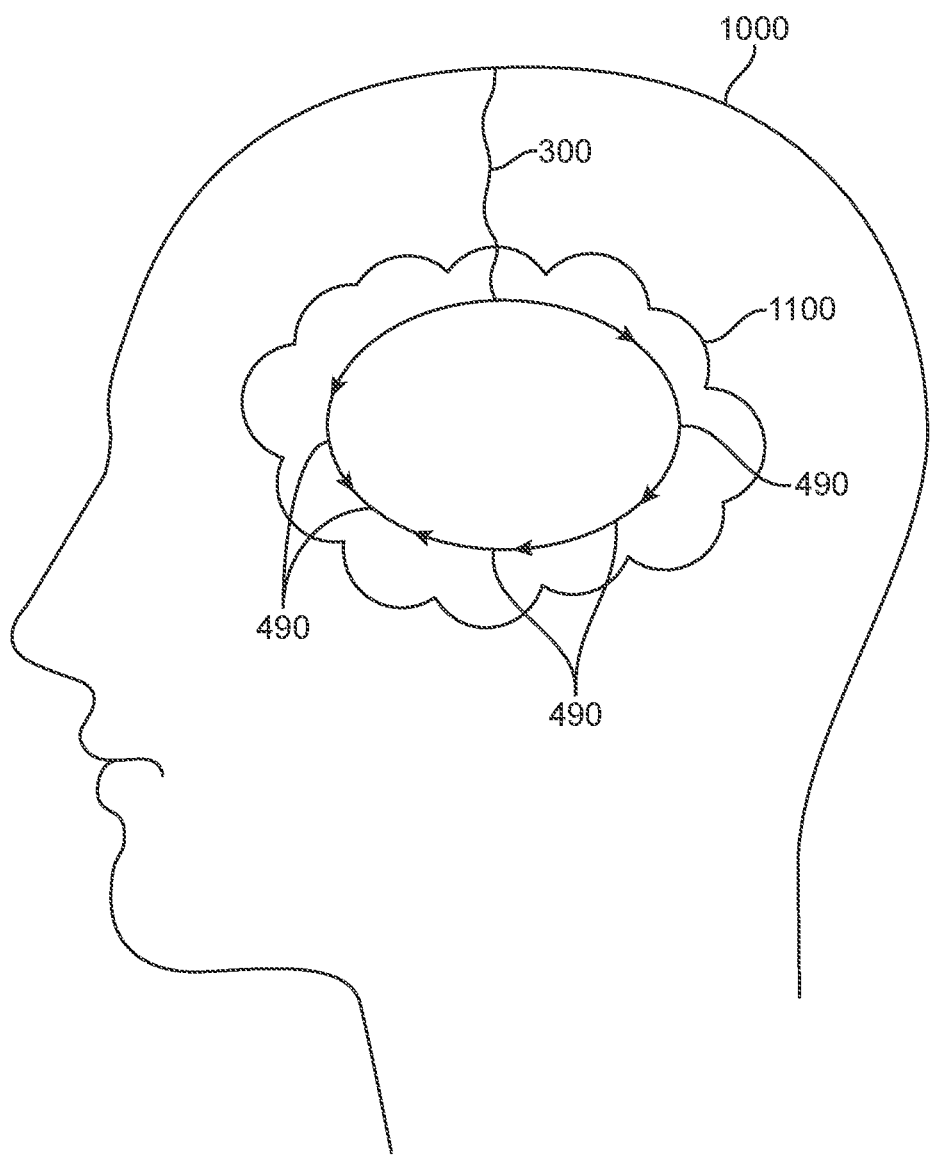
FIG. 18 illustrates another example of additional support elements in a tumor cavity.

FIG. 18 shows another example of the use of additional support elements 490 in the tumor cavity 1100 in the skull 1000 of patient. Again, a tether 300 provides power to an illumination element which may be any of the illumination elements disclosed herein. A plurality of additional support elements 490 may be coupled together (as indicated by the arrowheads) to form a fully closed loop or a partially open loop (if two dimensional), or a fully closed or partially open spheroid if three dimensional, that results in a rigid or semi-rigid structure that supports the tissue in the tumor cavity and prevents it from collapsing inward. Thus, customization is possible during surgery, ensuring that the light provided by the illumination element can illuminate the entire target treatment area and the cavity is supported. The support elements may snap together, press fit together, adhesively coupled together, or use coupling mechanisms known in the art to form any desired shape, and they support elements may be formed of an optical material to help distribute the light to the target treatment area.

Figure 19:
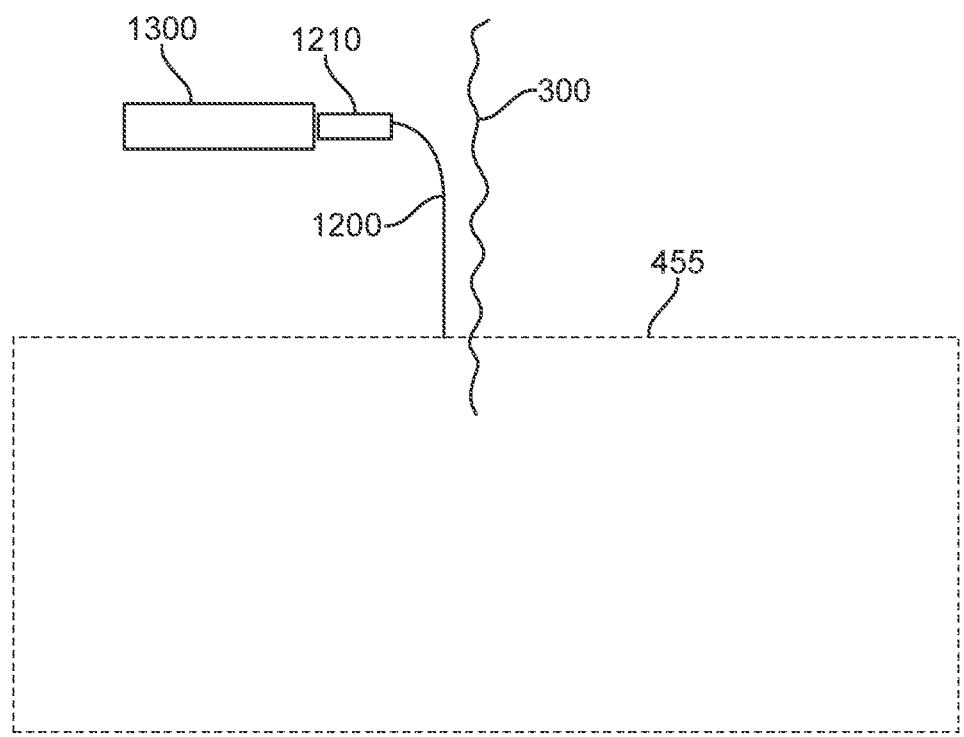
FIG. 19 illustrates a second port for coupling the illumination element with an external light source.

FIG. 19 illustrates a second port for coupling the illumination element with an external light source. Here, tether 300 couples the illumination element (not illustrated) disposed in a flat planar substrate 455 as described in FIG. 7 above. The tether 300 delivers power to the illumination element which delivers light via the flat planar substrate 455 to the target treatment area. As discussed above, the flat planar substrate 455 may be shaped and trimmed to conform to the target treatment area and it may be adhesively bonded to the tissue. In some cases, light may be used to help cure the adhesive such as when cyanoacrylate is used. Therefore, an external light source 1300 may provide the required curing light such as ultraviolet light via a port 1210 that may be releasably coupled with the external light source. The light is then delivered via an optical fiber 1200 to the flat planar substrate which then delivers the light to the target treatment area facilitating curing of the adhesive. Once the substrate 455 is adhesively bonded to the tissue, the external light source may be turned off and de-coupled from the second port 1210 and removed. The port 1210 and fiber 1200 may remain coupled to the flat planar substrate 455 or they may also be removed. Other components which may be adhesively bonded such as the supplemental support elements in FIGS. 17-18, the encapsulation surrounding the illumination element (e.g. in FIG. 5), optical lightguide shapes in FIGS. 6A-6D, and supplemental light guides in FIGS. 9A-9D may also be adhesively bonded and cured using the external light source coupled to light input port 1210 and delivered via optical fiber 1200 to the flat planar substrate for illuminating and curing the adhesive. In other examples, the second light port may be used to introduce light to the target treatment area via the substrate 455 using an external light source in order to illuminate biologicals, chemicals, or other agents that react to the light.

Figures 20A, 20B:
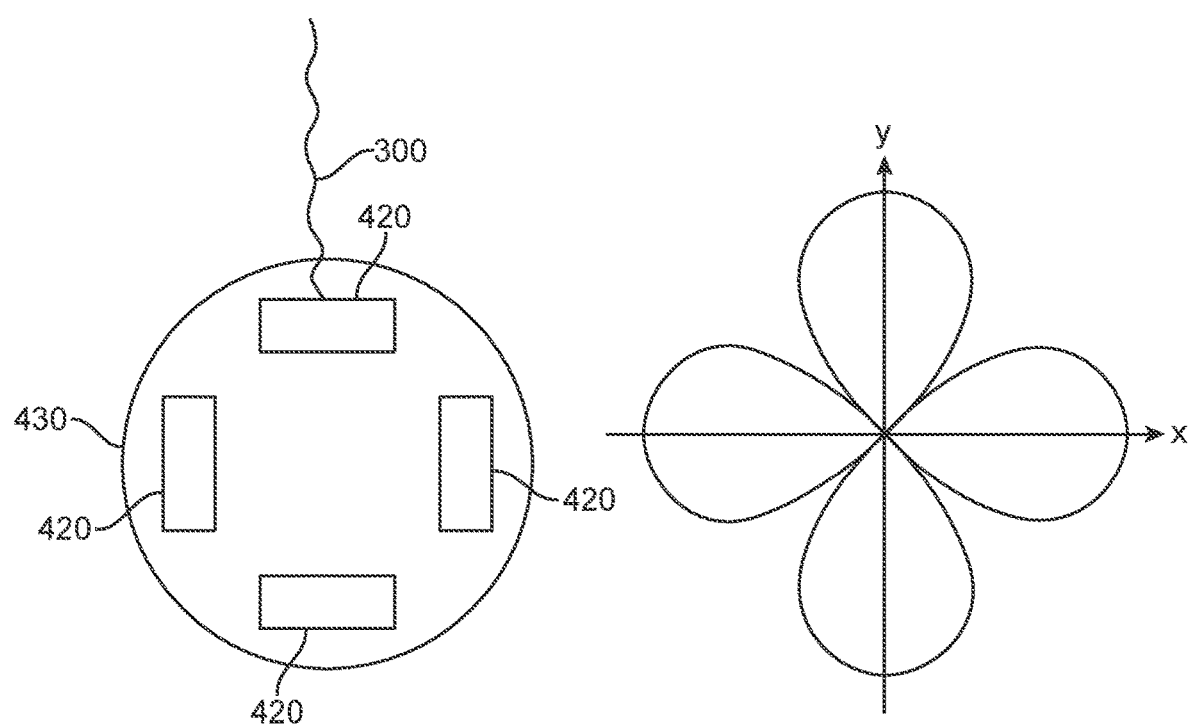
FIGS. 20A-20B illustrate the use of multiple light sources in the illumination element and the resulting illumination pattern.

FIGS. 20A-20B illustrate the use of multiple light sources in the illumination element and the resulting illumination pattern which provides desirable control of the illumination.

A uniform light source may not be an optimal solution for an asymmetrically distributed disease in human tissue. Depending on the individual patient and the particulars of the anatomy and tumor, there may be areas in the surgical cavity that will be more likely to contain residual tumor. It may be of benefit to concentrate light towards these areas in the interest of focusing the photodynamic therapy (PDT) effect. Clinical trials with intraoperative applications of PDT show a direct relationship between input light (fluence, Joules/cm^2) and clinical outcome. In a single application (as part of a longer series of treatments), the examples of devices disclosed herein can deliver a customized output of light, with greater emphasis/output towards areas of greater tumor risk.

The total amount of available light is limited in an implanted device, due largely to wireless power transfer limitations and tissue heating limitations. Therefore, optimal use of the light sources is desirable and may be accomplished in a device that can control the output of a plurality of lights in such as fashion as to have variable combinations of lights in an on vs. off configuration.

Furthermore, this configuration may also apply not only to on vs. off configurations but control of individual LED light output within a defined range. This can be controlled by firmware embedded within the implanted PCB or the ho using, which would direct the power output of individual lights in the implant. The control of this by the user may be accomplished through a user interface designed to control the power transfer and output device. Planning of this "prescription" for each patient can be analogous to the spatial and temporal planning of radiotherapy treatment, coupled with proscriptive imaging of tumor location in a patient.

In FIG. 20A, a tether 300 is coupled to the illumination element which in this example includes four independently controllable light sources 420, here LEDs. The LEDs are mounted in a substrate 430 such as a flexible PCB, and the assembly may be encapsulated in any manner, as previously described. Because the LEDs may be independently controlled, they may be turned on or off as needed in order to direct light in a desired direction for a desired amount of time.

FIG. 20B illustrates the intensity of the light in all four directions emitted by the four LEDs when light is emitted in a direction away from the center of the PCB 430. Each direction has a lobe shaped pattern showing the illumination pattern for each LED and the intensity of the light emitted. When the total power provided by the tether is fixed, the intensity of each LED is higher when only a single LED is activated at a time. Thus, illumination may be steered in a desired direction and light intensity may also be controlled.

Example of Method of Use

Figure 21:
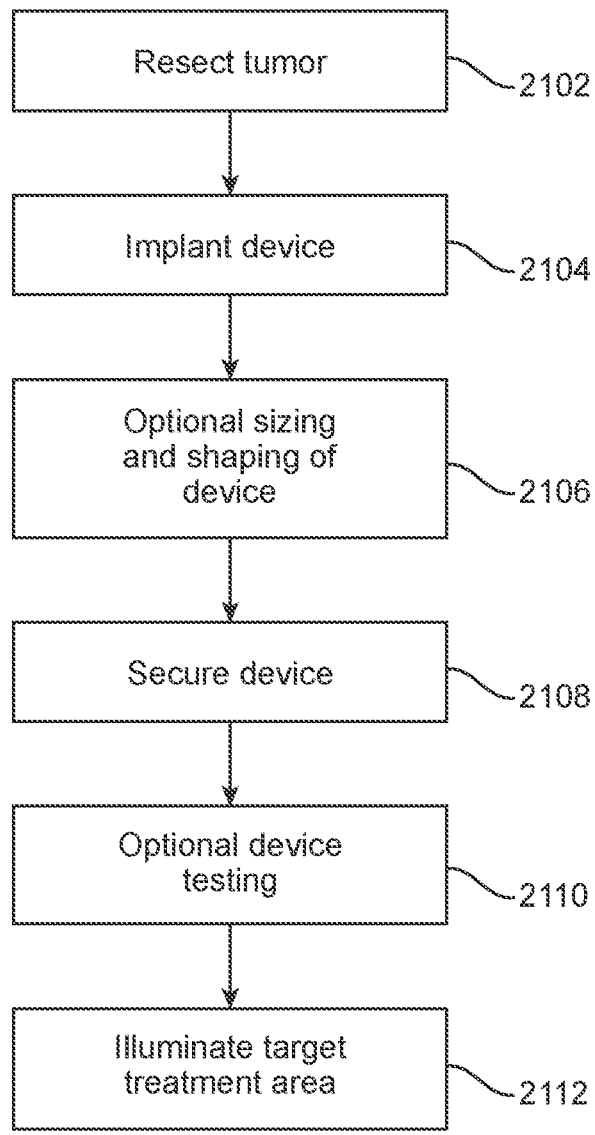
FIG. 21 shows an example of a method of treating a tumor.

FIG. 21 illustrates an example of a method of treating a tumor. The treatment may be determined by a team of physicians and surgeons which may include a neurosurgeon, neuroradiologist and a neurooncologist. Any of the illumination devices and optional features disclosed herein may be used according to the following method of use. This example is directed at treatment of brain cancer, but this is not intended to be limiting and one of skill in the art will appreciate that other diseases and conditions may also be treated.

MRI (magnetic resonance imaging) scans may be used to determine the size and shape of the tumor and based on that information, an appropriate size device may be selected. Other imaging techniques known in the art may also be used, such as computerized tomography (CT), positron emission tomography (PET), radiographic imaging, etc. The illumination dosage may also be determined based on the bioavailability of the photosensitizer delivered to target tissue, and efficacious light fluence and timing. In some examples, artificial intelligence (AI) or an AI classifier may be employed at least as a pattern recognition tool to detect and guide physicians towards an optimized targeted therapy to improve outcomes for patients. A dose includes photosensitizer drug dosage and frequency, as well as light fluence from the implantable phototherapy device. Initial dosage may be higher or lower depending on patient condition and expected severity of any remaining tumor cells in the tumor margins.

A craniotomy, often a 5-10 cm diameter circular section of bone is removed from the skull and allows access to the patient's brain. After the tumor has been resected 2102, the device is implanted 2104 in the tumor cavity formed after a craniotomy and tumor resection surgery, where the bulk of a glioblastoma tumor or other diseased tissue is removed by a neurosurgeon with standard surgical procedures. The light source portion of the device is secured in place by the neurosurgeon using methods known in the art including any of those described herein. The light source may comprise a thin, flexible sheet or wallpaper that is glued down in the cavity and cured in place. The surgeon can trim it to fit the individual patient's tumor size and shape 2106.

The surgeon may adhesively bond or otherwise secure the device into the tumor cavity 2108 using cyanoacrylate, fibrin glue or a similar biocompatible tissue adhesive. The device may be able to "self-cure" by emitting the wavelength of light required by the adhesive (glue). Either the LED emitter can be built-in to the device, or an external curing light can be coupled to the lightguide such that the curing light can reach where it needs to be. For example, if the adhesive is cured by light (e.g. UV curing adhesives), then the light source itself can be the source of its own curing light. The device may have an attachment that connects to one point on the light source and can transmit a curing light through the light source to the adhesive, such as the example previously described above with respect to FIG. 19.

If trimming is needed, the surgeon may trim the light source's lightguide shape to better fit the patient's individual tumor cavity with surgical scissors or other cutting instrument. The light source may contain visual markers that indicate areas that should not be cut.

Implantation of the illumination element is at the discretion of the neurosurgeon but should ensure that the light is directed at regions in the target treatment area that either contain residual tumor or are likely to experience recurrence. For GBM tumors which are dendritic and invasive, an additional margin up to about 2 cm from a known margin may be a good boundary. For smaller tumors, it may be possible to affix light elements such that all inner cavity surfaces are illuminated.

The device can then be tested 2110 to visually check that the light source is working and in the correct location.

The tether can extend to the outside of the skull, and the wireless power portion of the device is secured in place on the outside of skull and under the scalp, in any location, such as behind the ear. The tether may also be secured to the skull, so it does not get pulled out by the patient. A clip or grommet may be attached to the skull adjacent the craniotomy opening and the tether may be secured with the clip or grommet, serving to protect the wire from sharp edges around the craniotomy and also to hold the tether in place. Excess wire can be coiled around the clip or grommet. Additional suture, screws, adhesives, etc. may be used to help secure the tether and coil if needed. A recessed region in the skull may be formed to help accommodate the tether, coil, or housing thereby preventing or minimizing bulging. The coil may be disposed on the same side as the craniotomy or it may be disposed on the contralateral side. Once the device is implanted and secured to the skull, the skull may be closed, and the scalp also may be closed.

Optionally, the illumination system may include radiopaque markers adjacent the illumination element to permit the surgeon or physician to visualize and confirm placement of the device in the patient's tumor cavity using imaging techniques known in the art, such as MRI, PET, x-ray, etc.

After surgical recovery, photodynamic therapy is activated 2112 by powering the wireless power portion of the implant via an external transmitter in a clinic. The implant can control the power level it receives and directs the majority of that power to the light source. Dosing will be monitored by the transmitter, under the observance of a human operator. Sufficient dose for effective photodynamic therapy will be required for each session. As the sessions may be just a few hours at most, patients can take advantage of regular phototherapy sessions to control the recurrence of their tumor over months and even years. An example of a duty cycle may include one minute of illumination with thirty seconds without illumination, and then repeated. This helps reduce heat and also may allow the tissue to reoxygenate between light cycles. The power receiving element in any example of device may include a clock oscillator so that it can manage cycling of the light source. The energy transmitter may be able to reprogram the power receiver element to change the timing of the light delivery.

Fractionation of dose can occur over several days, distinguishing this method from one-time treatments.

Using the disclosed devices and methods allow transmission of significant power to the device efficiently while still having a light device in the center of the brain where traditional wireless power methods do not easily reach.

The phototherapy may optionally be combined with imaging and mapping to help direct the illumination. Since the illumination element may contain multiple light sources, steering of the light to a desired direction is possible so that if areas are identified having more tumor cells or expected to have more tumor cells, the phototherapy may be directed in that direction. Also, the phototherapy may be combined with algorithms and tumor recurrence modelling, to steer light to areas of concern with dosages also predicted by computer modelling. The devices, systems and methods described herein may be used with any photosensitizer that provides a desired diagnostic or therapeutic effect. Examples of photosensitizers are described below. The patient is then monitored for adverse reactions to the photodynamic therapy or the photosensitizer drug at regular intervals, e.g. every 3 to 6 months using brain imaging techniques known in the art to look for tumor recurrence. Patient dosages and therapy may be adjusted as needed.

Possible opportunities for personalizing treatment may occur at various times during the patient's therapy including during resection, during a recovery period of about 6 weeks after resection, during a combination of TMZ (Temozolomide) chemotherapy and radiotherapy for about 6 weeks, and during the six-month follow-up periods. Use of phototherapy may be used alone or in conjunction with any of these periods of time and treatment to provide an enhanced outcome.

Wavelength of Light

The wavelength of the light delivered by the illumination element is selected based on the wavelength required to activate the photosensitizer and depth of tissue penetration. For example, light in the red to near infrared wavelength range of about 600 nm to 940 nm may have sufficient tissue penetration in brain tissue. This wavelength may be used with any of the examples of devices disclosed herein.

Examples of Photosensitizers

Any photosensitizer which may have a therapeutic effect when exposed to light may be used with any of the examples of illumination systems described herein. Examples of photosensitizers include but are not limited to methyl aminolevulinate hydrochloride; padeliporfin potassium; talaporfin sodium; SGX-301; fimaporfin+gemcitabine; redaporfin; aminolaevulinic acid+artemisinin; CTT-1700; IVX-MES; IVX-PDT; IVXP-02; JL-103; Photobac; YC-9; ADC+fimaporfin; bleomycin sulfate+fimaporfin; lemuteporfin; methyl aminolevulinate hydrochloride; motexafin lutetium; padoporfin; SL-017; Vangiolux; Deuteporfin; Small Molecule to Activate ABCB1 for Graft Versus Host Disease; Recombinant Peptide to Target EGFR for Oncology; Small Molecules to Target eNOS; nNOS and NO Synthase for Oncology; epirubicin hydrochloride+fimaporfin; porfimer sodium; temoporfin; Palladium bacteriopheophorbide; rostaporfin; Verteporfin; and 5-Aminolevulinic acid.

These photosensitizers may be illuminated with light in the treatment of various cancers and other diseases including but not limited to Basal Cell Carcinoma (e.g. Basal Cell Epithelioma); Squamous Cell Carcinoma; Actinic (e.g.

Solar) Keratosis; Skin Cancer; Solid Tumor; Prostate Cancer; Esophageal Cancer; Transitional Cell Carcinoma (Urothelial Cell Carcinoma); Bile Duct Cancer (e.g. Cholangiocarcinoma); Endobronchial Cancer; Kidney Cancer (e.g. Renal Cell Cancer); Renal Cell Carcinoma; Choroidal Neovascularization; Brain Tumor; Glioma; Neurofibroma; Head And Neck Cancer; Hepatocellular Carcinoma; Metastatic Colorectal Cancer; Nasopharyngeal Cancer; Pancreatic Cancer; Benign Prostatic Hyperplasia; Age Related Macular Degeneration; Coronary Disease; Cutaneous Vascular Malformations; Peripheral Arterial Disease (PAD); Peripheral Vascular Disease (PVD); Mycosis Fungoides; Psoriasis; Glioblastoma Multiforme (e.g. GBM); Inflammatory Bowel Disease; Colorectal Cancer; Malignant Mesothelioma; Ovarian Cancer; Viral Infections; Colon Cancer; Graft Versus Host Disease (GVHD); Carcinomas; Sarcomas; Acne Vulgaris; Coronary Artery Disease (CAD) (e.g. Ischemic Heart Disease); Breast Cancer; Non-Small Cell Lung Cancer; Small-Cell Lung Cancer; and Bladder Cancer.

Experiments

A sample device having a coil for receiving RF energy, a rectifier for converting the alternating current of the power received into a direct current and LEDs was tested. The LEDs emitted light at about 630 nm wavelength and the fluence (energy density) was measured to be about 120 $J/cm^2$. Radiant power was measured using an optical power meter over a range of driving current from about 0.1 mA to about 20 mA. Based on the reported literature, this level of fluence is estimated to have an extrapolated necrosis death depth of about 10-20 mm.

The topic of photosensitizer drug activation is well understood in the art. The effective application of photodynamic therapy requires a light at an optimal wavelength of photosensitizer (PS) drug activation, at a sufficient intensity and for a sufficient duration of time to deliver a minimum light fluence (Joules per square centimeter of area).

Known experimental protocols have used light fluence as a controlled parameter (i.e., PS activation threshold or target) when demonstrating efficacy against tumors in pre-clinical and clinical testing. Therefore, because examples of the illumination systems disclosed herein deliver a discrete amount of light fluence consistent with what is known in the art, effective activation of PS must follow. In some examples, the target light fluence is 90-500 $J/cm^2$. In some examples, the target light fluence is optimized at 100-200 $J/cm^2$.

Fractionated or Metronomic PDT (mPDT) is of considerable interest in the PDT research community. mPDT may achieve the same doses for PS activation but over a longer period of time at low light intensity. The scientific literature has reported promising results with <100 $uW/cm^2$, 1000× less light intensity than typical PDT protocols, over a period of 10 days in an animal model. By using a much longer time period (1000×), the product of intensity multiplied by time remains constant.

Other literature suggests that fluence rate ($W/cm^2$) does have an impact, showing that with the same amount of dosage, a higher intensity kills tumor cells to a greater depth. It also can cause more death of normal cells, but this does support the notion of a "threshold" for activation of the photosensitizer.

Further literature also reports research with other light fluence rates are possible. Light fluence rates of 20-400 $J/cm^2$ were used (plurality between 100-200 $J/cm^2$), and there is some evidence that higher rates correspond to better outcomes.

Based on the data contained within these references, the implanted phototherapy device therapy targets 100 $J/cm^2$ of light fluence. When divided over many hours or even days, the instantaneous power required to deliver this energy can be on the order of mW or tens of mW (e.g. 7 $mW/cm^2$ over 4 hours). Additional details may be found in Brendan J. Quirk et al., "Photodynamic therapy (PDT) for malignant brain tumors—Where do we stand?" Photodiagnosis and Photodynamic Therapy 12.3 (2015): 530-544. As well as Tudge, S. H. et al, Modulation of light delivery in photodynamic therapy of brain tumours, Journal of Clinical Neuroscience, 1999 6(3), 227-232; and Yamagishi, Tissue-adhesive wirelessly powered optoelectronic device for metronomic photodynamic cancer therapy, Nature Biomedical Engineering, January 2019; the entire contents of which are incorporated herein by reference.

Notes and Examples

The following, non-limiting examples, detail certain aspects of the present subject matter to solve the challenges and provide the benefits discussed herein, among others.

Example 1 is an implantable phototherapy device, comprising: a power receiver element configured to receive power from an external power transmitter; a light delivery element powered by the power provided by the power receiver, and configured to deliver a phototherapy to a target treatment area; and a tether element operably coupled to the light delivery element and the power receiver element, the tether element configured to deliver the power from the power receiver element to the light delivery element.

Example 2 is the device of Example 1, wherein the power receiver element comprises a coil configured to receive the power from the external power transmitter, and wherein the power comprises radiofrequency energy.

Example 3 is the device of any of Examples 1-2, wherein the power receiver element comprises a sealed housing operably coupled with the tether, the device further comprising electronic components disposed in the sealed housing, the electronic components configured to control the power delivered to the light delivery element.

Example 4 is the device of any of Examples 1-3, wherein the light delivery element comprises a light source encapsulated in an optical material configured to protect the light source and wherein the optical material facilitates transmission of light from the light delivery element to the target treatment area.

Example 5 is the device of any of Examples 1-4, further comprising an optical lightguide coupled to the light delivery element, the optical lightguide shaped to facilitate delivery of light from the light delivery element to the target treatment area.

Example 6 is the device of any of Examples 1-5, wherein the light delivery element comprises a plurality of light sources disposed on a substrate, and wherein the substrate is configured to be shaped to match the target treatment area.

Example 7 is the device of any of Examples 1-6, wherein the substrate is a lightguide configured to direct light to the target treatment area and wherein the substrate is configured to be trimmed to a desired shape to fit the target treatment area.

Example 8 is the device of any of Examples 1-7, wherein the light delivery element comprises a plurality of light sources configured to be independently controllable relative to one another.

Example 9 is the device of any of Examples 1-8, wherein the light delivery element further comprises a temperature sensor configured to measure temperature at the target treatment area.

Example 10 is the device of any of Examples 1-9, wherein the light delivery element is disposed in a radially expandable member having an expanded configuration and a collapsed configuration, wherein in the expanded configuration the radially expandable member conforms to the target treatment area.

Example 11 is the device of any of Examples 1-10, wherein the light delivery element further comprises a port configured to releasably receive an optical fiber optically coupled to an external light source, and wherein light from the external light source is delivered to the light delivery element via the optical fiber for illumination of the target treatment area.

Example 12 is a phototherapy system comprising the device of any of Examples 1-11, and is the device of any of Examples 1-10, the external power transmitter configured to wirelessly transmit the power to the power receiver element.

Example 13 is the system of Example 12, further comprising a planar immersion lens disposed between the external power transmitter and the power receiver element, the planar immersion lens configured to focus energy from the external power transmitter toward the power receiver element.

Example 14 is the system of any of Examples 12-13, further comprising an electrode configured to provide electrical stimulation to the target treatment area.

Example 15 is the system of any of Examples 12-14, further comprising at least one support element, the support element configured to appose and support tissue in the target treatment area.

Example 16 is the system of any of Examples 12-15, further comprising a photosensitizer.

Example 17 is a method for delivering phototherapy to a target treatment region in a patient, the method comprising: providing an implantable phototherapy device comprising a power receiver element, a light delivery element, and a tether element; implanting the phototherapy device in a patient at the target treatment region; wirelessly transmitting power from an external power transmitter to the power receiver element; transferring the power from the power receiver element to the light delivery element via the tether; and illuminating the target treatment area with light from the light delivery element.

Example 18 is the method of Example 17, wherein wirelessly transmitting the power from the external power transmitter to the power receiver element comprises receiving radiofrequency energy with a coil.

Example 19 is the method of any of Examples 17-18, wherein the illuminating comprises illuminating the target treatment region with a plurality of light emitting elements that are independently controllable.

Example 20 is the method of any of Examples 17-19, wherein wirelessly transmitting the power comprises transmitting the power from the external power transmitter and focusing the power toward the power receiver element with a planar immersion lens.

Example 21 is the method of any of Examples 17-20, further comprising electrically stimulating tissue in the target treatment region with energy provided by an electrode adjacent the light delivery element.

Example 22 is the method of any of Examples 17-21, wherein the target treatment region comprises a brain of the patient.

Example 23 is the method of any of Examples 17-22, releasably coupling an optical fiber to the light delivery element; inputting light from an external light source to the light delivery element via the optical fiber; and illuminating the target tissue with the light from the external light source.

Example 24 is the method of any of Examples 17-23, wherein the light delivery element comprises a plurality of light sources disposed on a substrate, the method further comprising shaping the substrate to conform with the target treatment area and directing light in a plurality of directions to illuminate the target treatment area.

Example 25 is the method of any of Examples 17-24, further comprising trimming the substrate to a desired size or shape in order to fit in the target treatment area.

Example 26 is the method of any of Examples 17-25, further comprising measuring temperature at the target treatment area with a temperature sensor.

Example 27 is the method of any of Examples 17-26, wherein the light delivery element comprises a plurality of light sources encapsulated in an optical material, the optical material being a lightguide that directs light from the plurality of light sources to the target treatment area.

Example 28 is the method of any of Examples 17-27, wherein the light delivery element is disposed in a radially expandable member, the method further comprising radially expanding the radially expandable member to appose and conform with the target treatment area.

Example 29 is the method of any of Examples 17-28, further comprising disposing a support element in the target treatment area to help support tissue in the target treatment area to ensure the tissue is illuminated.

In Example 30, the devices, systems or methods of any one or any combination of Examples 1-29 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for delivering phototherapy to a target treatment region in a patient, the method comprising:
   providing an implantable phototherapy device comprising a power receiver element, a light delivery element, and a tether element;
   implanting the phototherapy device in a patient at the target treatment region;
   wirelessly transmitting power from an external power transmitter to the power receiver element, wherein wirelessly transmitting the power comprises transmitting the power from the external power transmitter and focusing the power toward the power receiver element with a planar immersion lens;
   transferring the power from the power receiver element to the light delivery element via the tether; and
   illuminating the target treatment area with light from the light delivery element.

2. The method of claim 1, wherein wirelessly transmitting the power from the external power transmitter to the power receiver element comprises receiving radiofrequency energy with a coil.

3. The method of claim 1, wherein the illuminating comprises illuminating the target treatment region with a plurality of light emitting elements that are independently controllable.

4. The method of claim 1, further comprising electrically stimulating tissue in the target treatment region with energy provided by an electrode adjacent the light delivery element.

5. The method of claim 1, wherein the target treatment region comprises a brain of the patient.

6. The method of claim 1, further comprising:
   releasably coupling an optical fiber to the light delivery element;
   inputting light from an external light source to the light delivery element via the optical fiber; and
   illuminating the target tissue with the light from the external light source.

7. The method of claim 1, wherein the light delivery element comprises a plurality of light sources disposed on a substrate, the method further comprising shaping the substrate to conform with the target treatment area and directing light in a plurality of directions to illuminate the target treatment area.

8. The method of claim 7, further comprising trimming the substrate to a desired size or shape in order to fit in the target treatment area.

9. The method of claim 1, wherein the light delivery element comprises a plurality of light sources encapsulated in an optical material, the optical material being a lightguide that directs light from the plurality of light sources to the target treatment area.

10. The method of claim 1, wherein the light delivery element is disposed in a radially expandable member, the method further comprising radially expanding the radially expandable member to appose and conform with the target treatment area.

11. The method of claim 1, wherein the light delivery element comprises an illumination element disposed in an optical light guide configured to facilitate distribution of the light to the target treatment area, and wherein the target treatment area comprises a cavity and the optical light guide is shaped to fit into the cavity and support tissue adjacent the cavity.

12. The method of claim 1, further comprising disposing a support element in the target treatment area to help support tissue in the target treatment area to ensure the tissue is illuminated.

* * * * *